(12) United States Patent
Maerki et al.

(10) Patent No.: US 10,865,182 B2
(45) Date of Patent: Dec. 15, 2020

(54) DIFLUOROKETAMIDE DERIVATIVES AS HTRA1 INHIBITORS

(71) Applicant: Hoffmann-La Roche Inc., Little Falls, NJ (US)

(72) Inventors: Hans P. Maerki, Basel (CH); Benoit Hornsperger, Altkirch (FR); Peter Mohr, Basel (CH); Michael Reutlinger, Freiburg (DE); Markus Rudolph, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/250,905

(22) Filed: Jan. 17, 2019

(65) Prior Publication Data
US 2019/0152895 A1  May 23, 2019

Related U.S. Application Data

(63) Continuation of application No. PCT/EP2017/067519, filed on Jul. 12, 2017.

(30) Foreign Application Priority Data

Jul. 18, 2016  (EP) .................... 16180013

(51) Int. Cl.
| | | |
|---|---|---|
| C07C 237/22 | (2006.01) | |
| C07C 255/54 | (2006.01) | |
| C07D 295/13 | (2006.01) | |
| C07D 213/65 | (2006.01) | |

(52) U.S. Cl.
CPC .......... *C07C 237/22* (2013.01); *C07C 255/54* (2013.01); *C07D 213/65* (2013.01); *C07D 295/13* (2013.01)

(58) Field of Classification Search
CPC .......................... C07C 237/22; C07D 295/13
See application file for complete search history.

(56) References Cited

U.S. PATENT DOCUMENTS

| | | | |
|---|---|---|---|
| 9,980,929 B2 * | 5/2018 | Hornsperger | ......... C07C 255/54 |
| 10,428,108 B2 * | 10/2019 | Hornsperger | ........ C07D 295/13 |
| 2005/0027101 A1 | 3/2005 | Gutheil et al. | |

FOREIGN PATENT DOCUMENTS

| | | |
|---|---|---|
| WO | 96/02499 A1 | 2/1996 |
| WO | 99/07734 A2 | 2/1999 |
| WO | 00/61542 A1 | 10/2000 |
| WO | 2005/035525 A2 | 4/2005 |
| WO | 2008/101160 A2 | 8/2008 |
| WO | 2012/093101 A1 | 7/2012 |
| WO | 2014/002053 A1 | 1/2014 |
| WO | 2016/135070 A1 | 9/2016 |
| WO | 2016/180751 A1 | 11/2016 |

OTHER PUBLICATIONS

Ammar, M., et al., "What's Ahead for the Treatment of Dry AMD" Review Ophthalmology 27(3):60-65 (Mar. 7, 2020) https://www.reviewofophthalmology.com/article/whats-ahead-for-the-treatment-of-dry-amd.

Bernstein, Peter R. et al., "Examination of Peptidic alpha-beta Diamino-alpha-alpha-difluoroketones as Inhibitors of human Leukocyte Elastase" Bioorganic and Medicinal Chemistry Letters (XP002768444), 4(18):2175-2178 (Oct. 1, 1994).

Cregge et al., "Inhibition of Human Neutrophil Elastase. 4. Design, Synthesis, X-ray Crystallographic Analysis, and Structure-Activity Relationships for a Series of P2-Modified, Orally Active Peptidyl Pentafluoroethyl Ketones" Journal of Medicinal Chemistry 41:2451-2480 (1998).

Derstine, C., et al., CAS Registry Database, 182001-67-8, 1996:494556 (Trifluoromethyl-Substituted Imidazolines: Novel Precursors of Trifluoromethyl Ketones Amenable to Peptide Synthesis), pgs. 1Other Date Nov. 13, 2019.

Doherty A. M. et al., "Design and Synthesis of Potent, Selective, and Orally Active Fluorine-Containing Renin Inhibitors" Journal of Medicinal Chemistry (XP002768443), 35:2-14 (Jan. 1, 1992).

Giovani, Simone et al., "Plasmodium falciparum subtilisin-like protease 1: discovery of potent difluorostatone-based inhibitors" RSC Advances (XP002768447), 5:22431-22448 (Feb. 19, 2015).

He, M., et al., "The Association Between Diabetes and Age-Related Macular Degeneration Among the Elderly in Taiwan" Diabetes Care 41:2202-2211 (Oct. 1, 2018).

International Preliminary Report on Patentability—PCT/EP2017/071019:pp. 1-8 (Mar. 7, 2019).

International Search Report—PCT/EP2017/071019:pp. 1-8 (Sep. 27, 2017).

ISR and Written Opinion for PCT/EP2017/054677 (dated Jul. 4, 2017).

ISR and Written Opinion for PCT/EP2017/054682 (dated May 4, 2017).

(Continued)

*Primary Examiner* — Golam M Shameem
(74) *Attorney, Agent, or Firm* — Bradley E. Davis

(57) ABSTRACT

The invention provides novel compounds having the general formula (I)

(I)

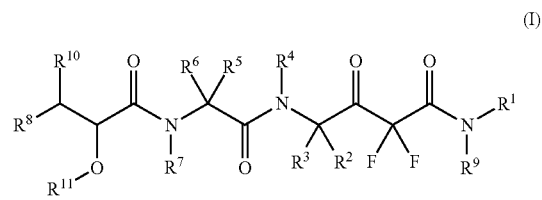

wherein $R^1$, $R^2$, $R^3$, $R^4$, $R^5$, $R^6$, $R^7$, $R^3$, $R^8$, $R^9$, $R^{10}$ and $R^{11}$ are as described herein, compositions including the compounds and methods of using the compounds.

28 Claims, No Drawings

(56) References Cited

OTHER PUBLICATIONS

Jacobo, Sarah Melissa P. et al., "Focus on Molecules: HtrA1 and neovascular AMD" Experimental Eye Research (XP028884160), 94(1):4-5 (2012).

Knobbe, C., et al., "Macular degeneration prevention" All About Vision (Article retrieved from.webpage: May 11, 2020; Last Update posted: Oct. 16, 2016),:1-12 (May 11, 2020) https://www.allaboutvision.com/conditions/amd-prevention.htm.

Perni et al., "Inhibitors of hepatitis C virus NS3.4A protease 2. Warhead SAR and optimization" Bioorganic & Medicinal Chemistry Letters 14(6):1441-1446 (2004).

Sasubilli, Ramakrishna et al., "General Inverse Solid-Phase Synthesis Method for C-Terminally Modified Peptide Mimetics" Journal of Combinatorial Chemistry (XP002522469), 6(6):911-915 (Nov. 1, 2004).

International Preliminary Report on Patentability (IPRP) for PCT/EP2017/067519 dated Jan. 22, 2019.

International Search Report for PCT/EP2017/067519 dated Aug. 14, 2017.

Skiles et al., "Inhibition of human leukocyte elastase by N-substituted peptides containing α,α-Difluorostatone residues at P1" J. Med. Chem. 35:4795-4808 (1992).

Truebestein et al., "Substrate-induced remodeling of the active site regulates human HTRA1 activity" Nat Structural Molec Biol, 18(3):386-388 (2011).

\* cited by examiner

DIFLUOROKETAMIDE DERIVATIVES AS HTRA1 INHIBITORS

CROSS-REFERENCE TO RELATED APPLICATIONS

This application is a continuation of International Application No. PCT/EP2017/067519, filed on Jul. 12, 2017, which claims priority from European Patent Application No. 16180013.1, filed on Jul. 18, 2016, the contents of which are incorporated herein by reference in their entireties.

The present invention relates to organic compounds useful for therapy or prophylaxis in a mammal, and in particular to serine protease HtrA1 inhibitors for the treatment or prophylaxis of HtrA1-mediated ocular diseases, such as wet or dry age-related macular degeneration, geographic atrophy, diabetic retinopathy, retinopathy of prematurity and polypoidal choroidal vasculopathy.

The present invention provides novel compounds of formula (I)

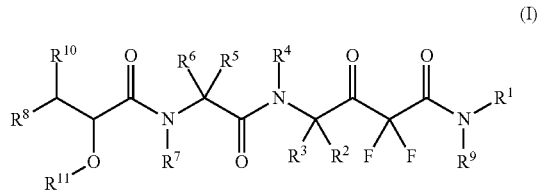

wherein
$R^1$ is selected from
i) $C_{1-6}$-alkyl,
ii) $C_{3-8}$-cycloalkyl substituted with $R^{24}$, $R^{25}$ and $R^{26}$,
iii) halo-$C_{1-6}$-alkyl,
iv) heterocycloalkyl-$C_{1-6}$-alkyl substituted with $R^{24}$, $R^{25}$ and $R^{26}$,
v) aryl-$C_{1-6}$-alkyl substituted with $R^{24}$, $R^{25}$ and $R^{26}$, and
vi) heteroaryl-$C_{1-6}$-alkyl substituted with $R^{24}$, $R^{25}$ and $R^{26}$;
$R^2$, $R^3$, $R^4$, $R^6$, $R^7$, $R^9$, $R^{10}$ and $R^{23}$ are independently selected from
i) H,
ii) $C_{1-6}$-alkyl, and
iii) $C_{3-8}$-cycloalkyl;
$R^5$ is selected from
i) aryl substituted with $R^{12}$, $R^{13}$ and $R^{14}$,
ii) aryl-$C_{1-6}$-alkyl substituted with $R^{12}$, $R^{13}$ and $R^{14}$,
iii) heteroaryl substituted with $R^{12}$, $R^{13}$ and $R^{14}$, and
iv) heteroaryl-$C_{1-6}$-alkyl substituted with $R^{12}$, $R^{13}$ and $R^{14}$;
$R^8$ is selected from
i) H,
ii) hydroxy,
iii) amino-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
iv) aminocarbonyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
v) aminocarbonyl-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
vi) carboxy,
vii) carboxy-$C_{1-6}$-alkyl,
viii) $C_{1-6}$-alkoxy,
ix) $C_{1-6}$-haloalkoxy,
x) $C_{1-6}$-alkoxycarbonyl,
xi) $C_{1-6}$-alkoxycarbonyl-$C_{1-6}$-alkyl,
xii) $C_{3-8}$-cycloalkyl,
xiii) aryl substituted with $R^{15}$, $R^{16}$ and $R^{17}$,
xiv) aryl-$C_{1-6}$-alkyl substituted with $R^{15}$, $R^{16}$ and $R^{17}$,
xv) aryl-$C_{1-6}$-alkoxy substituted with $R^{15}$, $R^{16}$ and $R^{17}$,
xvi) heteroaryl substituted with $R^{15}$, $R^{16}$ and $R^{17}$,
xvii) heteroaryl-$C_{1-6}$-alkyl substituted with $R^{15}$, $R^{16}$ and $R^{17}$, and
xviii) heteroaryl-$C_{1-6}$-alkoxy substituted with $R^{15}$, $R^{16}$ and $R^{17}$
xix) heterocycloalkyl substituted with $R^{15}$, $R^{16}$ and $R^{17}$,
xx) heterocycloalkyl-$C_{1-6}$-alkyl substituted with $R^{15}$, $R^{16}$ and $R^{17}$, and
xxi) heterocycloalkyl-$C_{1-6}$-alkoxy substituted with $R^{15}$, $R^{16}$ and $R^{17}$;
$R^{11}$ is selected from
i) amino-$C_{1-6}$-alkyl substituted on the nitrogen atom by $R^{21}$ and $R^{22}$,
ii) $C_{3-8}$-cycloalkyl substituted with $R^{18}$, $R^{19}$ and $R^{20}$,
iii) $C_{3-8}$-cycloalkyl-$C_{1-6}$-alkyl substituted with $R^{18}$, $R^{19}$ and $R^{20}$,
iv) $C_{3-8}$-cycloalkyl(halo)-$C_{1-6}$-alkyl substituted with $R^{18}$, $R^{19}$ and $R^{20}$,
v) aryl substituted with $R^{18}$, $R^{19}$ and $R^{20}$,
vi) aryl-$C_{1-6}$-alkyl substituted with $R^{18}$, $R^{19}$ and $R^{20}$,
vii) aryl-$C_{3-8}$-cycloalkyl substituted with $R^{18}$, $R^{19}$ and $R^{20}$,
viii) aryl-heterocycloalkyl substituted with $R^{18}$, $R^{19}$ and $R^{20}$,
ix) aryl(halo)-$C_{1-6}$-alkyl substituted with $R^{18}$, $R^{19}$ and $R^{20}$,
x) aryl(halo)-$C_{3-8}$-cycloalkyl substituted with $R^{18}$, $R^{19}$ and $R^{20}$,
xi) aryl(halo)-heterocycloalkyl substituted with $R^{18}$, $R^{19}$ and $R^{20}$,
xii) aryloxy-$C_{1-6}$-alkyl substituted with $R^{18}$, $R^{19}$ and $R^{20}$,
xiii) aryloxy-$C_{3-8}$-cycloalkyl substituted with $R^{18}$, $R^{19}$ and $R^{20}$,
xiv) aryloxy-heterocycloalkyl substituted with $R^{18}$, $R^{19}$ and $R^{20}$,
xv) aryloxy(halo)-$C_{3-8}$-cycloalkyl substituted with $R^{18}$, $R^{19}$ and $R^{20}$,
xvi) aryloxy(halo)-heterocycloalkyl substituted with $R^{18}$, $R^{19}$ and $R^{20}$,
xvii) aryloxy(halo)-$C_{1-6}$-alkyl,
xviii) heterocycloalkyl substituted with $R^{18}$, $R^{19}$ and $R^{20}$,
xix) heterocycloalkyl-$C_{1-6}$-alkyl substituted with $R^{18}$, $R^{19}$ and $R^{20}$,
xx) heterocycloalkyl-$C_{3-8}$-cycloalkyl substituted with $R^{18}$, $R^{19}$ and $R^{20}$,
xxi) heterocycloalkyl(halo)-$C_{3-8}$-cycloalkyl substituted with $R^{18}$, $R^{19}$ and $R^{20}$,
xxii) heterocycloalkyl(halo)-$C_{1-6}$-alkyl substituted with $R^{18}$, $R^{19}$ and $R^{20}$,
xxiii) heteroaryl substituted with $R^{18}$, $R^{19}$ and $R^{20}$,
xxiv) heteroaryl-$C_{1-6}$-alkyl substituted with $R^{18}$, $R^{19}$ and $R^{20}$, xxv) heteroaryl-$C_{3-8}$-cycloalkyl substituted with $R^{18}$, $R^{19}$ and $R^{20}$,
xxvi) heteroaryl(halo)-$C_{3-8}$-cycloalkyl substituted with $R^{18}$, $R^{19}$ and $R^{20}$,
xxvii) heteroaryl(halo)-$C_{1-6}$-alkyl substituted with $R^{18}$, $R^{19}$ and $R^{20}$,
xxviii) heteroaryloxy-$C_{1-6}$-alkyl substituted with $R^{18}$, $R^{19}$ and $R^{20}$,
xxix) heteroaryloxy-$C_{3-8}$-cycloalkyl substituted with $R^{18}$, $R^{19}$ and $R^{20}$,
xxx) heteroaryloxy(halo)-$C_{3-8}$-cycloalkyl substituted with $R^{18}$, $R^{19}$ and $R^{20}$, and
xxxi) heteroaryloxy(halo)-$C_{1-6}$-alkyl substituted with $R^{18}$, $R^{19}$ and $R^{20}$;
$R^{12}$, $R^{13}$, $R^{14}$, $R^{15}$, $R^{16}$, $R^{17}$, $R^{18}$, $R^{19}$, $R^{20}$, $R^{24}$, $R^{25}$ and $R^{26}$ are independently selected from
i) H,
ii) cyano,
iii) halogen,
iv) oxo,
v) $C_{1-6}$-alkyl,
vi) amino substituted on the nitrogen atom by two substituents independently selected from H, $C_{1-6}$-alkyl, $C_{1-6}$-alkoxycarbonyl, arylcarbonyl and heteroarylcarbonyl,
vii) amino-$C_{1-6}$-alkyl substituted on the nitrogen atom by two substituents independently selected from H, $C_{1-6}$-alkyl, $C_{1-6}$-alkoxycarbonyl, arylcarbonyl and heteroarylcarbonyl,
viii) $C_{1-6}$-alkyl,
ix) halo-$C_{1-6}$-alkyl,
x) $C_{3-8}$-cycloalkyl,
xi) $C_{1-6}$-alkoxycarbonyl-$C_{1-6}$-alkyl,
xii) carboxy-$C_{1-6}$-alkyl,
xiii) $C_{1-6}$-alkoxycarbonyl-$C_{1-6}$alkylaminocarbonyl-$C_{1-6}$alkyl,
xiv) carboxy-$C_{1-6}$-alkylaminocarbonyl-$C_{1-6}$alkyl,
xv) $C_{1-6}$-alkoxy,
xvi) halo-$C_{1-6}$-alkoxy,
xvii) $C_{1-6}$-alkoxycarbonyl-$C_{1-6}$-alkoxy,
xviii) carboxy-$C_{1-6}$-alkoxy,
xix) $C_{1-6}$alkoxycarbonyl-$C_{1-6}$alkylaminocarbonyl-$C_{1-6}$alkoxy, and
xx) carboxy-$C_{1-6}$alkylaminocarbonyl-$C_{1-6}$alkoxy;
xxi) heterocycloalkyl;
$R^{21}$ and $R^{22}$ are independently selected from
i) H,
ii) $C_{1-6}$-alkoxycarbonyl,
iii) carboxy-$C_{1-6}$-alkyl,
iv) arylcarbonyl, and
v) heteroarylcarbonyl;
or pharmaceutically acceptable salts;

Inhibition of the serine protease HtrA1, which belongs to an evolutionarily conserved family of HtrA proteins, has the potential to protect and treat tissue damage caused by the degeneration of retinal or photoreceptor cells in the human eye. The pathophysiological relevance of HtrA1 in the progression of the age-related macular degeneration has been firmly established by human genetic studies where a SNP in the HtrA1 promoter region results in increased HtrA1 transcript and protein levels. Age-related macular degeneration is the leading cause of severe irreversible central vision loss and blindness in individuals over 65 years of age in developed countries. There are two forms of AMD: dry AMD and wet AMD. Wet AMD (also known as exudative AMD), is associated with pathologic posterior choroidal neovascularization subsequent to the disruption of the delimiting Bruch's membrane. Tissue edema due to the leakage from the abnormal blood vessels damages the macula and impairs vision, eventually leading to blindness. In dry AMD, drusen have been reported in the macula of the eye, the cells in the macula die for the progressive accumulation of the drusen, resulting in progressive vision loss. Dry AMD is clinically described to occur in three stages: 1) early, 2) intermediate, and 3) advanced dry AMD. Dry AMD can also progress into wet AMD during any stage of the disease. Treatment strategies for wet AMD exists and the current standard of care is Lucentis (Genentech/Roche) and Eylea (Regeneron), an anti-VEGF antibody and an anti-VEGF trap injected intravitreally respectively. There are no current treatments for preventing loss of vision for the dry form and for preventing progression of dry AMD to local atrophy of the retinal tissue. As discussed above, HtrA1 risk alleles have been associated, with high statistical significance, with the AMD onsets and the protein has been reported to be present in drusen. These studies and further evidences provide relevance that HtrA1 is a fundamental factor involved in the pathophysiology and progression in AMD. This concept is further confirmed in different AMD disease models, where increased HtrA1 protein levels in the retina tissue have been shown to be responsible for the degradation of extracellular matrix (ECM) proteins like fibronectin, fibulins and aggrecan. The physiological balance between production and disintegration of the ECM components allows for both creation and maintenance of proper retina tissue architecture. Such balance has been reported to be lost in the progression of the age-related macular degeneration. In particular, the fibulins (mainly −3, −5, 31 6) have been reported to be important components of the Bruch's membrane in maintaining the integrity of elastic lamina and organization of the retina tissue overall. Several variants in fibulin 5 and fibulin 3 were reported to be associated with AMD. Missense mutations of the fibulin 5 gene have been associated with reduced secretion of fibulin 5. Different studies have reported that HtrA1 protease activity is directed to the cleavage of the fibulins as substrates. A direct inhibition of HtrA1 protease activity is expected to provide a protection reducing degradation of extracellular matrix proteins, in particular fibulins and fibrionectin, therefore preserving the retina tissue structure. The relevance of HtrA1's role in maintenance of the physiological homeostasis of the ECM components is firmly provided by the identification of human loss-of-function mutations causing familial ischemic cerebral small-vessel disease. The molecular mechanism underlies in the deficient TGFbeta inhibition by HtrA1 resulting in increased signaling levels, which in conjunction with deficient HtrA1-mediated degradation of various extracellular matrix components determine thickening of the intima responsible for the ischemic small-vessels. Given its fundamental role in regulating intracellular signaling pathways (e.g. TGFbeta) and the regulation of ECM proteins turnover, HtrA1 has been involved in several pathologies, as ocular diseases, rheumatoid arthritis, osteoarthritis, Alzheimer's disease, and some types of cancer.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of HtrA1, particularly in the treatment or prophylaxis of wet or dry age-related macular degeneration, geographic atrophy, diabetic retinopathy, retinopathy of prematurity and polypoidal choroidal vasculopathy.

The term "amino" denotes a —NH$_2$ group.

The term "amino-C$_{1-6}$-alkyl" denotes an C$_{1-6}$-alkyl group wherein one of the hydrogen atoms of the C$_{1-6}$-alkyl group has been replaced by an amino group. Examples of amino-C$_{1-6}$-alkyl groups are aminomethyl, aminoethyl or aminopropyl. Particular examples of amino-C$_{1-6}$-alkyl is aminomethyl.

The term "aminocarbonyl" denotes a group of the formula —C(O)—R', wherein R' is an amino group.

The term "aminocarbonyl-C$_{1-6}$-alkyl" denotes an C$_{1-6}$-alkyl group wherein one of the hydrogen atoms of the C$_{1-6}$-alkyl group has been replaced by an aminocarbonyl group. Examples of aminocarbonyl-C$_{1-6}$-alkyl groups are aminocarbonylmethyl, aminocarbonylethyl or aminocarbonylpropyl The term "C$_{1-6}$-alkoxy" denotes a group of the formula —O—R', wherein R' is an C$_{1-6}$-alkyl group. Examples of C$_{1-6}$-alkoxy groups include methoxy, ethoxy, n-propoxy, isopropoxy, n-butoxy, isobutoxy and tert-butoxy. Particular example is methoxy. In the case of R$^{12}$, particular example is methoxy.

The term "C$_{1-6}$-alkoxycarbonyl" denotes a group of the formula —C(O)—R', wherein R' is a C$_{1-6}$-alkoxy group. Particular example of C$_{1-6}$-alkoxycarbonyl is a group wherein R' is tert-butoxy.

The term "C$_{1-6}$-alkoxycarbonyl-C$_{1-6}$-alkoxy" denotes an C$_{1-6}$-alkoxy group wherein one of the hydrogen atoms of the C$_{1-6}$-alkoxy group has been replaced by a C$_{1-6}$-alkoxycarbonyl group. Particular example of C$_{1-6}$-alkoxycarbonyl-C$_{1-6}$-alkoxy is a methoxy wherein one of the hydrogen atoms has been replaced by tert-butoxycarbonyl.

The term "C$_{1-6}$-alkoxycarbonyl-C$_{1-6}$-alkyl" denotes an C$_{1-6}$-alkyl group wherein one of the hydrogen atoms of the C$_{1-6}$-alkyl group has been replaced by a C$_{1-6}$-alkoxycarbonyl group. Particular example of C$_{1-6}$-alkoxycarbonyl-C$_{1-6}$-alkyl is a methyl wherein one of the hydrogen atoms has been replaced by tert-butoxycarbonyl.

The term "C$_{1-6}$alkoxycarbonyl-C$_{1-6}$alkylaminocarbonyl-C$_{1-6}$alkoxy" denotes an C$_{1-6}$-alkoxy group wherein one of the hydrogen atoms of the C$_{1-6}$-alkoxy group has been replaced by a C$_{1-6}$alkoxycarbonyl-C$_{1-6}$alkylaminocarbonyl group. Particular example is methoxy wherein one of the hydrogen atoms has been replaced by ter-butoxycarbonylmethylamino.

The term "C$_{1-6}$alkoxycarbonyl-C$_{1-6}$alkylaminocarbonyl-C$_{1-6}$alkyl" denotes an C$_{1-6}$-alkyl group wherein one of the hydrogen atoms of the C$_{1-6}$-alkyl group has been replaced by a C$_{1-6}$alkoxycarbonyl-C$_{1-6}$alkylaminocarbonyl group. Particular example is methyl wherein one of the hydrogen atoms has been replaced by ter-butoxycarbonylmethylaminocarbonyl.

The term "C$_{1-6}$alkoxycarbonyl-C$_{1-6}$alkylaminocarbonyl" denotes a group of the formula —C(O)—R', wherein R' is a C$_{1-6}$alkoxycarbonyl-C$_{1-6}$alkylamino group. Particular example is a group wherein R' is ter-butoxycarbonylmethylamino.

The term "C$_{1-6}$-alkoxycarbonyl-C$_{1-6}$-alkylamino" denotes a group of the formula —NH—R', wherein R' is an C$_{1-6}$-alkoxycarbonyl-C$_{1-6}$-alkyl group. Particular example is a group wherein R' is ter-butoxycarbonylmethyl.

The term "C$_{1-6}$-alkoxycarbonyl-C$_{1-6}$-alkyl" denotes an C$_{1-6}$-alkyl group wherein one of the hydrogen atoms of the C$_{1-6}$-alkyl group has been replaced by an C$_{1-6}$-alkoxycarbonyl group. Particular example is a methyl wherein one of the hydrogen atoms of has been replaced by a ter-butoxycarbonyl.

The term "C$_{1-6}$-alkyl" denotes a monovalent linear or branched saturated hydrocarbon group of 1 to 6 carbon atoms. Examples of C$_{1-6}$-alkyl include methyl, ethyl, propyl, isopropyl, n-butyl, iso-butyl, sec-butyl, tert-butyl and pentyl. Particular C$_{1-6}$-alkyl groups are methyl and isopropyl. In the case of R$^2$, particular example is isopropyl.

The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "aryl(halo)-C$_{1-6}$-alkyl" denotes a halo-C$_{1-6}$-alkyl group wherein one of the hydrogen atoms of the halo-C$_{1-6}$-alkyl group has been replaced by an aryl group. Particular examples are groups wherein the aryl group is phenyl. Further particular example is phenyl-difluoromethyl.

The term "aryl-C$_{1-6}$-alkyl" denotes an —C$_{1-6}$-alkyl group wherein one of the hydrogen atoms of the C$_{1-6}$-alkyl group has been replaced by an aryl group. Particular aryl-C$_{1-6}$-alkyl group is phenyl-C$_{1-6}$-alkyl. Further particular examples of aryl-C$_{1-6}$-alkyl are phenylmethyl and phenylpropyl. Furthermore particular examples of aryl-C$_{1-6}$-alkyl is phenylmethyl.

The term "aryl-C$_{1-6}$-alkoxy" denotes an —C$_{1-6}$-alkoxy group wherein one of the hydrogen atoms of the —C$_{1-6}$-alkoxy group has been replaced by an aryl group. Particular examples are groups wherein the aryl group is phenyl. Particular aryl-C$_{1-6}$-alkoxy group is phenylmethoxy.

The term "aryloxy" denotes a group of the formula —O—R', wherein R' is an aryl group. Particular examples of aryloxy group are groups wherein R' is phenyl.

The term "aryloxy-C$_{1-6}$-alkyl" denotes an C$_{1-6}$-alkyl group wherein one of the hydrogen atoms of the C$_{1-6}$-alkyl group has been replaced by an aryloxy group. Particular examples are groups wherein the aryloxy group is phenoxy. Further particular example of aryloxy-C$_{1-6}$-alkyl is phenoxyalkyl. Further particular example is phenoxymethyl.

The term "aryloxy(halo)-C$_{1-6}$-alkyl" denotes a halo-C$_{1-6}$-alkyl group wherein one of the hydrogen atoms of the halo-C$_{1-6}$-alkyl group has been replaced by an aryloxy group. Particular examples are groups wherein the aryloxy group is phenoxy.

The term "arylcarbonyl" denotes a group of the formula —C(O)—R', wherein R' is an aryl group. Particular example is a group wherein R' is phenyl.

The term "aryl(halo)-C$_{3-8}$-cycloalkyl" denotes a halo-C$_{3-8}$-cycloalkyl group wherein one of the hydrogen atoms of the halo-C$_{3-8}$-cycloalkyl group has been replaced by an aryl group. Particular examples are groups wherein the aryl group is phenyl. Further particular example is phenyl-difluorocyclopropyl.

The term "aryl-C$_{3-8}$-cycloalkyl" denotes a halo-C$_{3-8}$-cycloalkyl group wherein one of the hydrogen atoms of the C$_{3-8}$-cycloalkyl group has been replaced by an aryl group. Particular examples are groups wherein the aryl group is phenyl. Further particular example is phenylcyclopropyl.

The term "aryloxy-C$_{3-8}$-cycloalkyl" denotes a C$_{3-8}$-cycloalkyl group wherein one of the hydrogen atoms of the C$_{3-8}$-cycloalkyl group has been replaced by an aryloxy group. Particular examples are groups wherein the aryloxy group is phenoxy. Further particular example is phenyl-difluorocyclopropyl.

The term "aryloxy(halo)-C$_{3-8}$-cycloalkyl" denotes a halo-C$_{3-8}$-cycloalkyl group wherein one of the hydrogen atoms of the halo-$C_{3-8}$-cycloalkyl group has been replaced by an aryloxy group. Particular examples are groups wherein the aryloxy group is phenoxy. Further particular example is phenoxy-difluorocyclopropyl.

The term "aryloxy-$C_{3-8}$-cycloalkyl" denotes a $C_{3-8}$-cycloalkyl group wherein one of the hydrogen atoms of the $C_{3-8}$-cycloalkyl group has been replaced by an aryloxy group. Particular examples are groups wherein the aryloxy group is phenoxy. Further particular example is phenoxy-cyclopropyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "carboxy" denotes a —COOH group.

The term "carboxy-$C_{1-6}$-alkoxy" denotes an $C_{1-6}$-alkoxy group wherein one of the hydrogen atoms of the $C_{1-6}$-alkoxy group has been replaced by a carboxy group. Particular example is carboxymethoxy.

The term "carboxy-$C_{1-6}$-alkyl" denotes an $C_{1-6}$-alkyl group wherein one of the hydrogen atoms of the $C_{1-6}$-alkyl group has been replaced by a carboxy group. Particular example is carboxymethyl.

The term "carboxy-$C_{1-6}$-alkylaminocarbonyl-$C_{1-6}$alkoxy" denotes an $C_{1-6}$-alkoxy group wherein one of the hydrogen atoms of the $C_{1-6}$-alkoxy group has been replaced by a carboxy-$C_{1-6}$alkylaminocarbonyl group. Particular example is carboxymethylaminocarbonylmethoxy.

The term "carboxy-$C_{1-6}$alkylaminocarbonyl-$C_{1-6}$alkyl" denotes an $C_{1-6}$-alkyl group wherein one of the hydrogen atoms of the $C_{1-6}$-alkyl group has been replaced by a carboxy-$C_{1-6}$alkylaminocarbonyl group. Particular example is carboxymethylaminocarbonylmethyl.

The term "carboxy-$C_{1-6}$alkylaminocarbonyl group" denotes a group of the formula —C(O)—R', wherein R' is a carboxy-$C_{1-6}$alkylamino group. Particular example is carboxymethylamino.

The term "carboxy-$C_{1-6}$alkylamino" denotes a group of the formula —NH—R', wherein R' is a carboxy-$C_{1-6}$alkyl group. Particular example is a group wherein R' is carboxymethyl.

The term "cyano" denotes a —C≡N group.

The term "$C_{3-8}$-cycloalkyl" denotes a monovalent saturated monocyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Particular monocyclic cycloalkyl groups are cyclopropyl, cyclobutanyl, cyclopentyl and cyclohexyl. More particular monocyclic cycloalkyl group is cyclopropyl.

The term "$C_{3-8}$-cycloalkyl(halo)-$C_{1-6}$-alkyl" denotes a halo-$C_{1-6}$-alkyl group wherein one of the hydrogen atoms of the halo-$C_{1-6}$-alkyl group has been replaced by an $C_{3-8}$-cycloalkyl group.

The term "$C_{3-8}$-cycloalkyl-$C_{1-6}$-alkyl" denotes an —$C_{1-6}$-alkyl group wherein one of the hydrogen atoms of the $C_{1-6}$-alkyl group has been replaced by an $C_{3-8}$-cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Particular examples of cycloalkylalkyl are cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Further particular examples cycloalkylalkyl is cyclohexylethyl.

The term "halo-$C_{1-6}$-alkoxy" denotes an $C_{1-6}$-alkoxy group wherein at least one of the hydrogen atoms of the $C_{1-6}$-alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups is difluoromethoxy.

The term "halo-$C_{1-6}$-alkyl" denotes an $C_{1-6}$-alkyl group wherein at least one of the hydrogen atoms of the $C_{1-6}$-alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoroethyl.

The term "halo-$C_{3-8}$-cycloalkyl" denotes an $C_{3-8}$-cycloalkyl group wherein at least one of the hydrogen atoms of the $C_{3-8}$-cycloalkyl group has been replaced by the same or different halogen atoms.

The term "halogen" and "halo" are used interchangeably herein and denote fluoro, chloro, bromo or iodo. Particular halogen is chloro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, and benzothiophenyl. Particular heteroaryl groups are pyrazinyl, pyridinyl, pyrimidinyl and thiophenyl. In the case of substituent $R^{11}$, particular heteroaryl groups are pyrazinyl, pyridinyl, pyrimidinyl and thiophenyl, more particularly pyridinyl.

The term "heteroaryl(halo)-$C_{1-6}$-alkyl" denotes a halo-$C_{1-6}$-alkyl group wherein one of the hydrogen atoms of the halo-$C_{1-6}$-alkyl group has been replaced by a heteroaryl group.

The term "heteroaryl-$C_{1-6}$-alkyl" denotes an $C_{1-6}$-alkyl group wherein one of the hydrogen atoms of the $C_{1-6}$-alkyl group has been replaced by a heteroaryl group.

The term "heteroaryl-$C_{1-6}$-alkoxy" denotes an $C_{1-6}$-alkoxy group wherein one of the hydrogen atoms of the $C_{1-6}$-alkoxy group has been replaced by a heteroaryl group.

The term "heteroaryloxy" denotes a group of the formula —O—R', wherein R' is a heteroaryl group.

The term "heteroaryloxy-$C_{1-6}$-alkyl" denotes an $C_{1-6}$-alkyl group wherein one of the hydrogen atoms of the $C_{1-6}$-alkyl group has been replaced by anheteroaryloxy group.

The term "heteroaryloxy(halo)-$C_{1-6}$-alkyl" denotes a halo-$C_{1-6}$-alkyl group wherein one of the hydrogen atoms of the halo-$C_{1-6}$-alkyl group has been replaced by a heteroaryloxy group.

The term "heteroarylcarbonyl" denotes a group of the formula —C(O)—R', wherein R' is a heteroaryl group. Particular heteroarylcarbonyl is a group wherein R' is pyridinyl.

The term "heteroaryl(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by a heteroaryl group.

The term "heteroaryl-$C_{3-8}$-cycloalkyl" denotes a halo-$C_{3-8}$-cycloalkyl group wherein one of the hydrogen atoms of the $C_{3-8}$-cycloalkyl group has been replaced by a heteroaryl group.

The term "heteroaryloxy-$C_{3-8}$-cycloalkyl" denotes a $C_{3-8}$-cycloalkyl group wherein one of the hydrogen atoms of the $C_{3-8}$-cycloalkyl group has been replaced by a heteroaryloxy group.

The term "heteroaryloxy(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by a heteroaryloxy group.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydrooxazolyl, tetrahydro-pyridinyl, or dihydropyranyl.

The term "heterocycloalkyl-$C_{1-6}$-alkyl" denotes an $C_{1-6}$-alkyl group wherein one of the hydrogen atoms of the $C_{1-6}$-alkyl group has been replaced by a heterocycloalkyl group. In the case of $R^1$, particular heterocycloalkyl-$C_{1-6}$-alkyl is morpholinoethyl.

The term "heterocycloalkyl-$C_{1-6}$-alkoxy" denotes an $C_{1-6}$-alkoxy group wherein one of the hydrogen atoms of the $C_{1-6}$-alkoxy group has been replaced by a heterocycloalkyl group.

The term "heterocycloalkyl(halo)-$C_{1-6}$-alkyl" denotes a halo-$C_{1-6}$-alkyl group wherein one of the hydrogen atoms of the halo-$C_{1-6}$-alkyl group has been replaced by a heterocycloalkyl group.

The term "heterocycloalkyl(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by a heterocycloalkyl group.

The term "hydroxy" denotes a —OH group.

The term "oxo" denotes a =O group.

The term "phenoxy" denotes a group of the formula —O—R', wherein R' is a phenyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

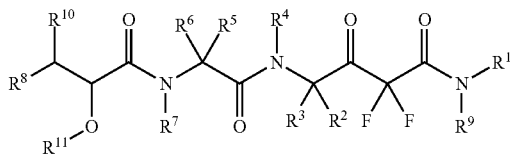 ⇌ 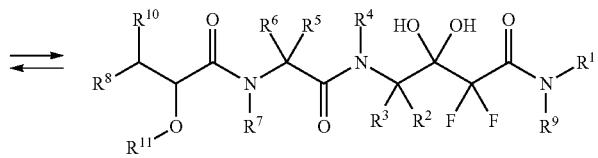

Depending on the individual compound and the conditions it has been exposed, the $CF_2$-ketone moieties in compounds I exist in part, mainly or totally in form of its hydrate. Thus, any description of a $CF_2$-ketone moiety always describes both ketone and hydrate form.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Another embodiment of the present invention are compounds according to formula (I) as described herein, wherein
  $R^1$ is selected from
    i) $C_{1-6}$-alkyl, and
    ii) heterocycloalkyl-$C_{1-6}$-alkyl substituted with $R^{24}$, $R^{25}$ and $R^{26}$;
  $R^2$ is $C_{1-6}$-alkyl;
  $R^3$, $R^4$, $R^6$, $R^7$, $R^9$ and $R^{10}$ are H;
  $R^5$ is selected from
    i) phenyl substituted with $R^{12}$, $R^{13}$ and $R^{14}$, and
    ii) phenyl-$C_{1-6}$-alkyl substituted with $R^{12}$, $R^{13}$ and $R^{14}$,
  $R^8$ is phenyl substituted with $R^{15}$, $R^{16}$ and $R^{17}$;
  $R^{11}$ is selected from
    i) phenyl substituted with $R^{18}$, $R^{19}$ and $R^{20}$, and
    ii) pyridinyl substituted with $R^{18}$, $R^{19}$ and $R^{20}$;
  $R^{12}$ is selected from
    i) H, and
    ii) $C_{1-6}$-alkoxy;
  $R^{13}$, $R^{14}$, $R^{17}$ and $R^{20}$ are H;
  $R^{15}$ is selected from
    i) H,
    ii) cyano, and
    iii) halogen;
  $R^{16}$ is selected from
    i) H, and
    ii) halogen;
  $R^{18}$ is selected from
    i) halogen, and
    ii) cyano;
  $R^{19}$ is selected from
    i) H,
    ii) cyano,
    iii) $C_{1-6}$-alkyl, and
    iv) halogen;
  or pharmaceutically acceptable salts.

Another particular embodiment of the present invention are compounds according to formula (I) as described herein, wherein $R^1$ is selected from
  i) $C_{1-6}$-alkyl, and
  ii) heterocycloalkyl-$C_{1-6}$-alkyl substituted with $R^{24}$, $R^{25}$ and $R^{26}$.

A furthermore particular embodiment of the present invention are compounds according to formula (I) as described herein, wherein $R^1$ is halo-$C_{1-6}$-alkyl.

A furthermore particular embodiment of the present invention are compounds according to formula (I) as described herein, wherein $R^1$ is trifluoroethyl.

Another particular embodiment of the present invention are compounds according to formula (I) as described herein, wherein $R^2$ is $C_{1-6}$-alkyl.

Also a furthermore particular embodiment of the present invention are compounds according to formula (I) as described herein, wherein $R^2$ is isopropyl.

A particular embodiment of the present invention are compounds according to formula (I) as described herein, wherein $R^3$ is H.

A particular embodiment of the present invention are compounds according to formula (I) as described herein, wherein $R^4$ is H.

A particular embodiment of the present invention are compounds according to formula (I) as described herein, wherein $R^6$ is H.

A particular embodiment of the present invention are compounds according to formula (I) as described herein, wherein $R^7$ is H.

A particular embodiment of the present invention are compounds according to formula (I) as described herein, wherein $R^9$ is H.

A particular embodiment of the present invention are compounds according to formula (I) as described herein, wherein $R^{10}$ is H.

A further particular embodiment of the present invention are compounds according to formula (I) as described herein, wherein $R^3$, $R^4$, $R^6$, $R^7$, $R^9$ and $R^{10}$ are H.

A particular embodiment of the present invention are compounds according to formula (I) as described herein, wherein $R^5$ is selected from
  i) phenyl substituted with $R^{12}$, $R^{13}$ and $R^{14}$, and
  ii) phenyl-$C_{1-6}$-alkyl substituted with $R^{12}$, $R^{13}$ and $R^{14}$.

In a further particular embodiment of the present invention are compounds according to formula (I) as described herein, wherein $R^5$ is phenyl-$C_{1-6}$-alkyl substituted with $R^{12}$, $R^{13}$ and $R^{14}$.

A more particular embodiment of the present invention are compounds according to formula (I) as described herein, wherein $R^5$ is phenyl substituted with one $C_{1-6}$-alkoxy.

A particular embodiment of the present invention are compounds according to formula (I) as described herein, wherein $R^8$ is phenyl substituted with $R^{15}$, $R^{16}$ and $R^{17}$.

A further particular embodiment of the present invention are compounds according to formula (I) as described herein, wherein $R^8$ is selected from
  i) hydroxy, and
  ii) phenyl substituted with $R^{15}$, $R^{16}$ and $R^{17}$.

A more particular embodiment of the present invention are compounds according to formula (I) as described herein, wherein $R^8$ is phenyl substituted with $R^{15}$, $R^{16}$ and $R^{17}$.

Another embodiment of the present invention are compounds according to formula (I) as described herein, wherein $R^{11}$ is selected rom
i) phenyl substituted with $R^{18}$, $R^{19}$ and $R^{20}$, and
ii) pyridinyl substituted with $R^{18}$, $R^{19}$ and $R^{20}$.

A more particular embodiment of the present invention are compounds according to formula (I) as described herein, wherein $R^{11}$ is phenyl substituted with $R^{18}$, $R^{19}$ and $R^{20}$.

Another embodiment of the present invention are compounds according to formula (I) as described herein, wherein $R^{12}$ is selected from
i) H, and
ii) $C_{1-6}$-alkoxy.

Another particular embodiment of the present invention are compounds according to formula (I) as described herein, wherein $R^{12}$ is $C_{1-6}$-alkoxy.

Another embodiment of the present invention are compounds according to formula (I) as described herein, wherein $R^{13}$, $R^{14}$, $R^{17}$ and $R^{20}$ are H.

Also an embodiment of the present invention are compounds according to formula (I) as described herein, wherein $R^5$ is selected from
i) H,
ii) cyano, and
iii) halogen.

A further particular embodiment of the present invention are compounds according to formula (I) as described herein, wherein $R^{15}$ is halogen.

Another embodiment of the present invention are compounds according to formula (I) as described herein, wherein $R^{16}$ is selected from
i) H, and
ii) halogen.

Another particular embodiment of the present invention are compounds according to formula (I) as described herein, wherein $R^{16}$ is H.

Another embodiment of the present invention are compounds according to formula (I) as described herein, wherein $R^{18}$ is selected from
i) halogen, and
ii) cyano.

Another particular embodiment of the present invention are compounds according to formula (I) as described herein, wherein $R^{19}$ is selected from
i) cyano, and
ii) halogen.

Particular examples of compounds of formula (I) as described herein are selected from (S)-4-((S)-2-((R)-2-(3,5-dichlorophenoxy)-3-phenylpropanamido)-3-phenylpropanamido)-2,2-difluoro-5-methyl-3-oxo-N-(2,2,2-trifluoroethyl)hexanamide;

(S)-4-((S)-2-((R)-2-(3,5-dichlorophenoxy)-3-phenylpropanamido)-2-phenylacetamido)-2,2-difluoro-5-methyl-N-(2-morpholinoethyl)-3-oxohexanamide;

(S)-4-((S)-2-((R)-2-(3,5-dichlorophenoxy)-3-phenylpropanamido)-2-(4-methoxyphenyl)acetamido)-2,2-difluoro-5-methyl-3-oxo-N-(2,2,2-trifluoroethyl)hexanamide;

(S)-4-((S)-2-((R)-3-(3-chlorophenyl)-2-(3,5-dichlorophenoxy)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3-chloro-5-methylphenoxy)-3-(3-chlorophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3-chlorophenoxy)-3-(3,4-dichlorophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((R)-3-(3-chlorophenyl)-2-(3,5-dicyanophenoxy)propanamido)-2-(4-methoxyphenyl)acetamido)-2,2-difluoro-5-methyl-3-oxo-N-(2,2,2-trifluoroethyl)hexanamide;

(S)-4-((S)-2-((R)-3-(3-chlorophenyl)-2((5-chloropyridin-3-yl)oxy)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3-chlorophenoxy)-3-(3,5-dichlorophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((S)-3-(3-chlorophenyl)-2-(3,5-dichlorophenoxy)propanamido)-2-(4-methoxyphenyl)acetamido)-2,2-difluoro-5-methyl-3-oxo-N-(2,2,2-trifluoroethyl)hexanamide;

(S)-4-((S)-2-((S)-3-(3-chlorophenyl)-2-(3,5-dichlorophenoxy)propanamido)-2-phenylacetamido)-2,2-difluoro-5-methyl-3-oxo-N-(2,2,2-trifluoroethyl)hexanamide;

(S)-4-((S)-2-((R)-2-(3-chloro-5-cyanophenoxy)-3-(3-chlorophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3-chloro-5-cyanophenoxy)-3-(3-chlorophenyl)propanamido)-2-phenylacetamido)-2,2-difluoro-5-methyl-3-oxo-N-(2,2,2-trifluoroethyl)hexanamide;

(4S)-4-((2S)-2-(2-(3-chloro-5-cyanophenoxy)-3-(3-cyanophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3,5-dicyanophenoxy)-3-(3-fluorophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3-cyanophenoxy)-3-(3-fluorophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3-chlorophenoxy)-3-(3-fluorophenyl)propanamido)-2-(4-methoxyphenyl)acetamido)-2,2-difluoro-5-methyl-3-oxo-N-(2,2,2-trifluoroethyl)hexanamide;

and pharmaceutically acceptable salts thereof.

Processes for the manufacture of compounds of formula (I) as described herein are an object of the invention.

Synthesis

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereomers is produced during a reaction, these enantiomers or diastereomers can be separated by methods described herein or known to the man skilled in the art such as, e.g., chromatography on a chiral column or crystallization. The substituents and indices used in the following description of the processes have the significance given herein.

The following abbreviations are used in the present text:
BOC=t-butyloxycarbonyl, DBU=2,3,4,6,7,8,9,10-octahydro-pyrimido[1,2-a]azepine, DCE=1,2-dichloroethane, DCM=dichloromethane, DEAD=diethyl-azodicarboxylate, DIAD=diisopropyl-azodicarboxylate, DCC=N,N'-dicyclohexylcarbodiimide, DMAP=4-dimethylaminopyridine, DMF=N,N-dimethylformamide, EDCI=N-(3-dimethylaminopropyl)-N'-ethylcarbodiimide hydrochloride, eq.=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=iPr$_2$NEt=N-ethyl diisopropylamine, LAH=lithium aluminum hydride, PG=protecting group, rt=room temperature, TBAF=tetrabutylammonium fluoride, TBDMS=t-butyldimethylsilyl, TBME=t-butyl methyl ether, TBTU=O-benzotriazol-1-yl-N,N,N',N'-tetramethyl-uronium tetrafluoroborate, TEA=Et$_3$N=triethylamine, TFA=trifluoroacetic acid, THF=tetrahydrofuran, quant.=quantitative.

The synthesis of compounds of the general formula I can be accomplished according to scheme 1. An appropriately protected (e. g., with a BOC-group) α-amino-aldehyde 1 is reacted with the Reformatsky reagent derived from ethyl 2-bromo-2,2-difluoroacetate 2 to provide, under chelation control, amino-hydroxy-ester 3 (scheme 1, step a). The latter is transformed into amide 5 by treatment with the necessary amine 4 at elevated temperature, typically in boiling methanol (scheme 1, step b). Conventional deprotection, in the case of a BOC group with, e.g., TFA in DCM or anhydrous HCl in dioxane or a mixture of dioxane and MeOH, delivers free amine 6 (scheme 1, step c) which can then be elongated with the appropriate, suitably protected—e. g., with a BOC-group-amino acid 7 under standard peptide coupling conditions, e. g., with HATU or TBTU, and an appropriate base, e. g., Huenig's base or TEA, in an inert solvent like DMF to key intermediate 8 (scheme 1, step d). Deprotection as above delivers amino-alcohol 9 (scheme 1, step e) which is ready for coupling with acid 10 (for its synthesis, see below), again under standard peptide coupling conditions to furnish penultimate intermediate 11 (scheme 1, step f). Eventually, oxidation, e. g., with Dess Martin periodinane, in an inert solvent like DCM or a mixture of DCM and THF as solubilizing agent, generates the final target molecule I. Starting aldehyde 1, which is prone to racemization—in case one of $R^2$ or $R^3$ is hydrogen—is prepared as described in literature from the corresponding Weinreb amide by reduction with LAH and used immediately for the next step (J. Med. Chem. 1992, 35, 4795-4808).

Scheme 1

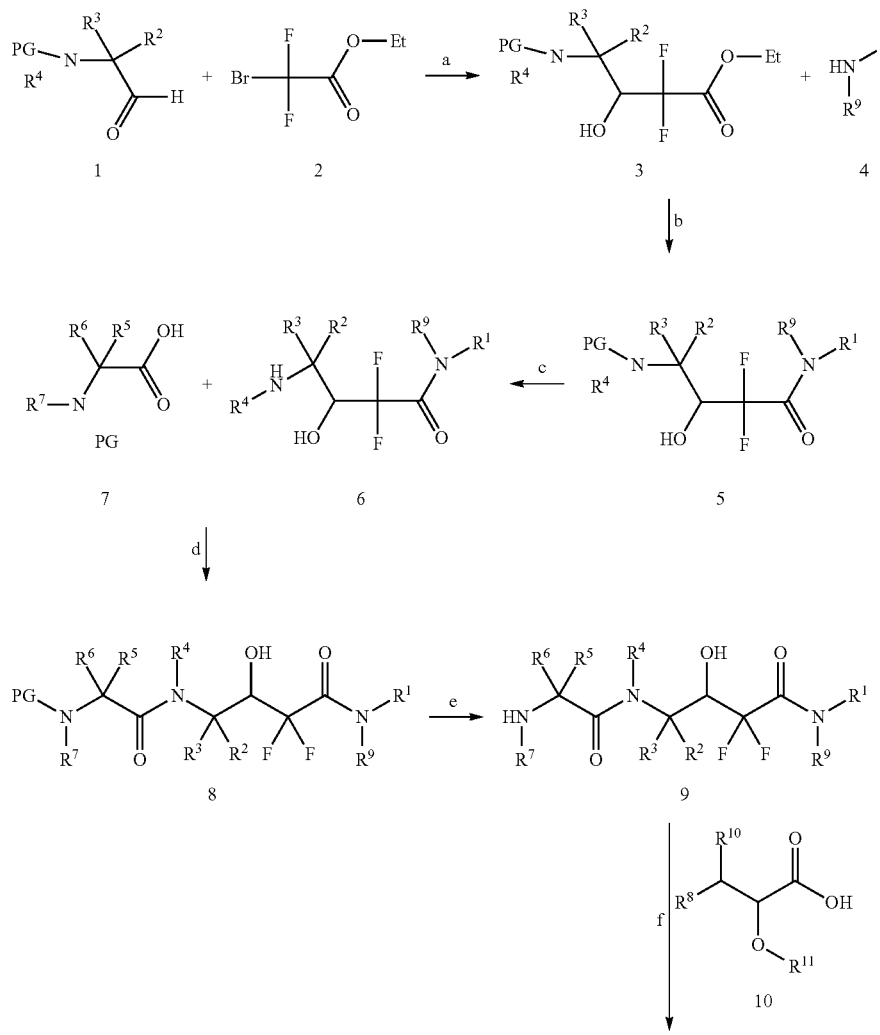

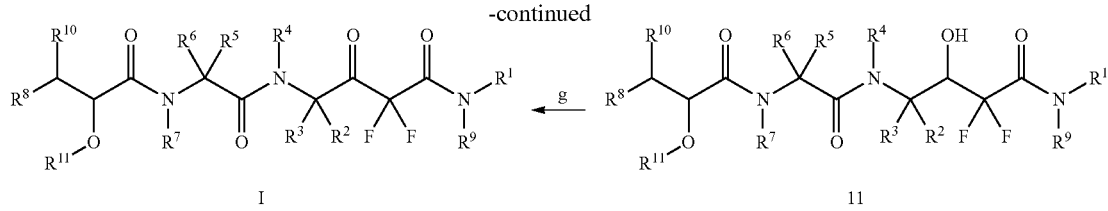

Building block 10 used in scheme 1 can be synthesized as summarized in scheme 2. The appropriate, commercially available Grignard-reagent 1 is reacted with epoxy-ester 2 in a regio- and stereoselective manner to deliver α-hydroxy ester 3, typically under copper catalysis, e.g., copper bromide dimethyl sulfide, in an inert solvent like THF, in a temperature range of −78° C. to −20° C. Ensuing etherification is accomplished by treating the latter with a phenolic compound 4 under typical Mitsunobu-conditions, e. g., DIAD or DEAD and triphenylphosphine, in an inert solvent like THF, in a temperature range of −20° C. to RT. In case 10 is used as homochiral alcohol, this reaction takes place under clean inversion. Careful hydrolysis under standard conditions, e. g., LiOH in a mixture of water, MeOH or EtOH, and THF, in a temperature range of −20° C. to RT, delivers building block 10 without erosion of the stereochemical integrity.

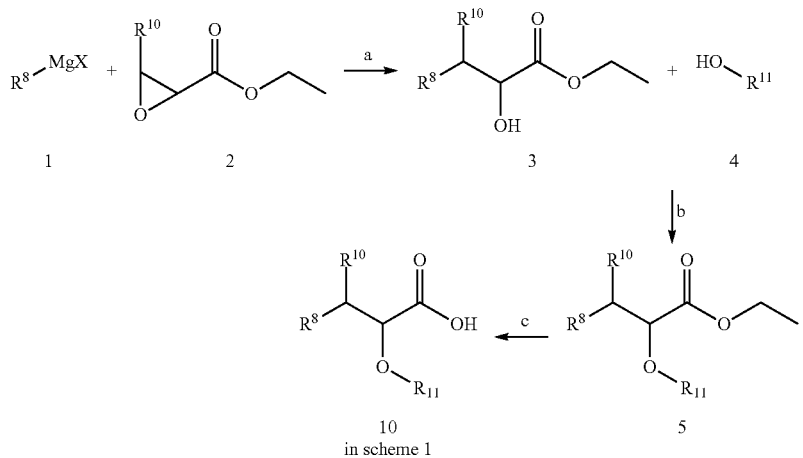

In case $R^{11}$ is an optionally substituted alkyl group, it is introduced by classical alkylation with the appropriate halide, preferably an iodide, and a base, e.g., NaH or KOtBu, in a polar aprotic solvent like DMF, acetone, or acetonitrile, as indicated in scheme 3.

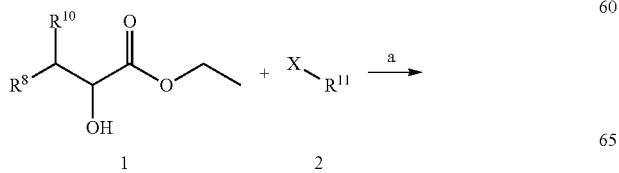

-continued

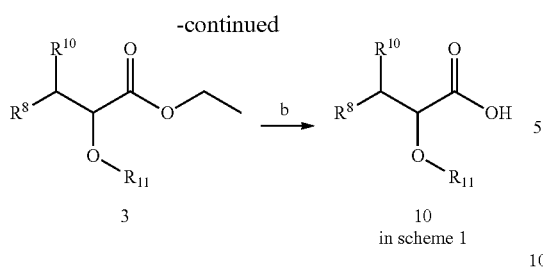

In another embodiment, or if residue $R^8$ contains functional groups not compatible with a metallorganic reagent, compound 10 in scheme 1 can be prepared as outlined in scheme 4.

Also an embodiment of the present invention is a process to prepare a compound of formula (I) as defined above comprising i) the reaction of a compound of formula (III) with a compound of formula (IV)

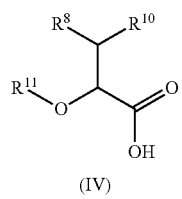

Scheme 4

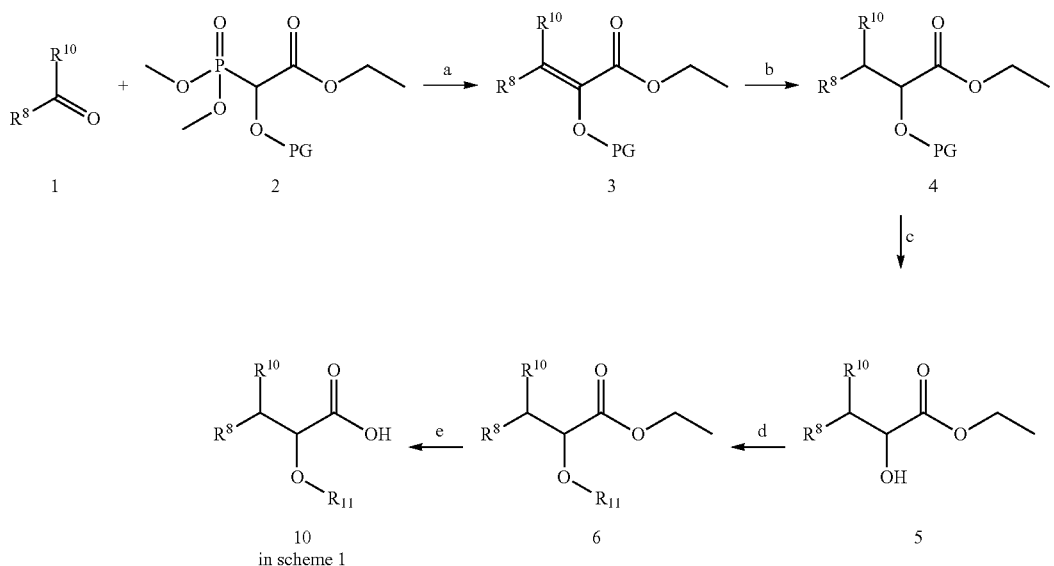

Aldehyde or ketone 1 is reacted with a suitably protected, e.g., as TBDMS-ether, Wittig-Horner reagent 2 in the presence of a base like KOtBu or NaH in an inert solvent like THF or DMF in a temperature range between −20° C. and RT to afford enolether 3 as E/Z-mixture (scheme 4, step a). Hydrogenation under standard conditions, e. g. with 10% Pd on charcoal, in a solvent like EtOH, MeOH, or AcOEt at ambient temperature and atmospheric pressure delivers intermediate 4 (scheme 4, step b), which is then deprotected to deliver free alcohol 5 (scheme 4, step c). In the case of a silylether, TBAF treatment in THF is well suited. Ensuing etherification is accomplished by treatment with a phenolic compound 6 under typical Mitsunobu-conditions, e. g., DIAD or DEAD and triphenylphosphine, in an inert solvent like THF, in a temperature range of −20° C. to RT (scheme 4, step d). Standard hydrolysis as above, e. g., with LiOH in a mixture of water, MeOH or EtOH, and THF, in a temperature range of −20° C. to RT, generates finally building block 10 (scheme 4, step e). By applying in step b a chiral catalyst, it is in principle possible to prepare also by this route 4, 5, 6, and 7 as pure enantiomers.

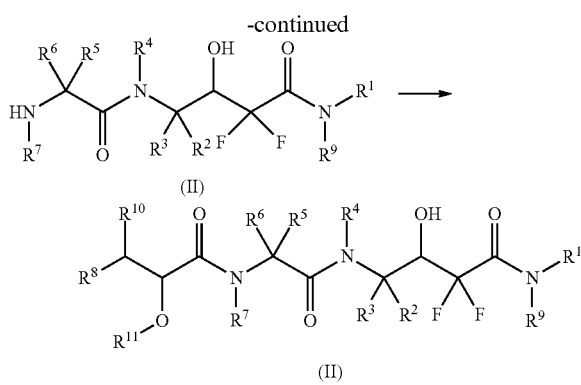

In particular, in the presence of a base such as diisopropylamine, and in the presence of a coupling reagent, such as HATU, in a solvent like DMF between 0° C. and room temperature.

then ii) the reaction of a compound of formula (II) in oxidative conditions

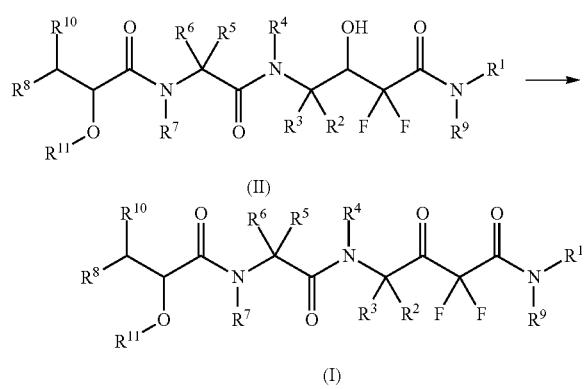

In particular, in the presence of 1,1,1-triacetoxy-1,1-dihydro-1,2-benziodoxol-3(1H)-one (Dess-Martin periodane), in a solvent like DCM between 0° C. and room temperature.

wherein $R^1$, $R^2$, $R^3$, $R^4$, $R^5$, $R^6$, $R^7$, $R^3$, $R^8$, $R^9$, $R^{10}$ and $R^{11}$ are as defined above.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of ocular diseases, in particular HtrA1-mediated ocular diseases, more particularly wet or dry age-related macular degeneration, geographic atrophy, diabetic retinopathy, retinopathy of prematurity or polypoidal choroidal vasculopathy.

In a particular embodiment, the compounds of formula (I) or their pharmaceutically acceptable salts and esters can be used for the treatment or prophylaxis of wet or dry age-related macular degeneration, geographic atrophy, diabetic retinopathy, retinopathy of prematurity or polypoidal choroidal vasculopathy.

The present invention also relates to the use of a compound according to formula (I) as described herein for the preparation of a medicament for the treatment or prophylaxis of wet or dry age-related macular degeneration, geographic atrophy, diabetic retinopathy, retinopathy of prematurity and polypoidal choroidal vasculopathy.

Also an object of the invention is a method for the treatment or prophylaxis of wet or dry age-related macular degeneration, geographic atrophy, diabetic retinopathy, retinopathy of prematurity and polypoidal choroidal vasculopathy, which method comprises administering an effective amount of a compound according to formula (I) as described herein.

Also an embodiment of the present invention are compounds of formula (I) as described herein, when manufactured according to any one of the described processes.

Assay Procedures

Protein Purification for Use in Enzymatic Assays

Human HtrA1 protein comprising the catalytic and the PDZ domain from amino acid Asp161 up to Pro480 was expressed in BL21(DE3) cells as an N-terminal fusion protein with a 6× His-SUMO tag. The transformed cells were grown in LB medium at 37° C. until the optical density at 600 nm was between 0.6 and 0.8. Then, the temperature was decreased to 18° C. and the recombinant protein production induced by adding IPTG to a final concentration of 250 mM. Fermentation was performed over night at 18° C.

The protein was purified to homogeneity following a four-step procedure. 40 g of cells were suspended in 50 mM HEPES pH 7.8, 250 mM NaCl, 10 mM $MgCl_2$, 0.35% CHAPS, 10% glycerol containing 20 tabs per liter of EDTA-free cOmplete Protease Inhibitor (Roche) as well as 30 mg/l DNAse and Rnase. The cells were broken by a single passage through a homogenizer at 750 bar and then centrifuged at 20'000×g for 30 minutes. The clear supernatant was applied on a triple 5 ml HisTrap column (GE Healthcare) equilibrated in 50 mM HEPES pH 7.8, 500 mM NaCl, 0.35% CHAPS, 10% glycerol. After washing with stepwise increasing concentrations of imidazole (20 mM, 40 mM, 50 mM) HtrA1 fusion protein was eluted within a linear gradient from 10 to 100% of the same buffer containing 500 mM imidazole. HtrA1 containing fractions were pooled, concentrated and then applied to a Superdex S200 prep grade (XK26/100 GE Healthcare) column equilibrated in 50 mM ethanolamine pH 9.6, 500 mM NaCl, 0.35% CHAPS, 10% glycerol, 0.02% sodium azide. In order to cleave the SUMO fusion protein and to release active HtrA1, the pooled fractions from the size exclusion chromatography were blended with SUMO protease (Life Technologies) and incubated ca. 20 hours at RT. HtrA1 was isolated out of the reaction solution by chromatography on a Superdex S200 prep grade (XK26/100—GE Healthcare) column equilibrated 50 mM ethanolamine pH 9.6, 500 mM NaCl, 0.35% CHAPS, 10% glycerol, 0.02% sodium azide. Fractions containing active HtrA1 were pooled and concentrated. Following the above strategy 150 mg of the HtrA1 (catalytical domain/PDZ construct) could be purified. As shown by RP-HPLC and SDS-PAGE, >98% pure protein was obtained.

HtrA1 Enzyme Inhibition Assay

Enzyme activity is measured by observing the increase in fluorescence intensity caused by cleavage of a peptide substrate containing a fluorophore, whose emission is quenched in the intact peptide.

Assay buffer: 500 mM Tris pH 8.0, 200 mM NaCl, 0.025% CHAPS, 0.005% BSG

Enzyme: human HtrA1 Cat-PDZ, final concentration 1 nM

Substrate: Mca-Ile-Arg-Arg-Val-Ser-Tyr-Ser-Phe-Lys (Dnp)-Lys, final concentration 500 nM (from Innovagen Cat: SP-5076-1, Lot: 89584.02)

Mca=(7-Methoxycoumarin-4-yl)acetyl

Dnp=2,4-Dinitrophenyl

Final volume: 51 µl

Excitation 320 nm, emission 390 nm

After a pre-incubation of the HtrA1 protease for 30 min with compounds, substrate is added to the wells and initial RFU is measured. Upon incubation for 2 hours at RT, the enzymatic activity cleaved the substrate releasing fluorescent Mca-peptide conjugate and the final RFU value is measured. The presence of inhibitors leads to a decreased final RFU.

For the analysis $\Delta RFU$ is calculated as $RFU_{end} - RFU_{start}$ and then percent inhibition is calculated with the following formula:

$$PCT\_Inhibition = 100 - 100 * (\Delta RFU_{compound} - \Delta RFU_{blank})/(\Delta RFU_{negctrl} - \Delta RFU_{blank})$$

where neg.ctrl is protease with substrate and DMSO blank is as neg.ctrl without protease compound is as neg.ctrl with test compounds at desired concentration The $IC_{50}$ is determined using a 4-point Hill-fit equation where x=concentration of test compound A=extrapolated value of the curve at effector concentration equals 0

B=extrapolated value of the curve at effector concentration equals infinite

C=concentration at the inflection point of the sigmoidal curve ($IC_{50}$)

D=Hill coefficient of slope at the inflection point of the fitted curve $$Y(x) = A + \frac{B - A_D}{1 + \left(\frac{C}{x}\right)}$$

As a counter screen the compounds are added to the protease-substrate reaction mix only after 2 h incubation, when all the substrate is turned over, to identify autofluorescent or absorbing compounds giving false positive hits.

| Example | IC50 (μM) |
|---|---|
| 1 | 0.006590 |
| 2 | 0.007115 |
| 3 | 0.002085 |
| 4 | 0.000917 |
| 5 | 0.001280 |
| 6 | 0.000985 |
| 7 | 0.001088 |
| 8 | 0.000838 |
| 9 | 0.002830 |
| 10 | 0.001750 |
| 11 | 0.001470 |
| 12 | 0.000711 |
| 13 | 0.000293 |
| 14 | 0.001760 |
| 15 | 0.001050 |
| 16 | 0.000686 |
| 17 | 0.000461 |

Compounds of formula (I) and their pharmaceutically acceptable salts or esters thereof as described herein have $IC_{50}$ values between 0.00001 μM and 1000 μM, particular compounds have $IC_{50}$ values between 0.0001 μM and 500 μM, further particular compounds have $IC_{50}$ values between 0.0001 μM and 50 μM, more particular compounds have $IC_{50}$ values between 0.0001 μM and 5 μM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations; lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg, can be administered either by single dose per day or per week, or by multiple doses (2 to 4) per day, or by multiple doses per week. In case of parenteral application, such as intramuscularly, intravenously, or intraocularly, the formulation can contain 0.001% to 15% by weight of medicament and the required dose, which can be between 0.01 and 25 mg, can be administered either by single dose per day, per week or per month, or by multiple doses (2 to 4) per day, or by multiple doses per week or per month. It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Abbreviations: aq.=aqueous; CAS-RN=Chemical Abstracts Service Registry Number; HPLC=high performance liquid chromatography; MS=mass spectrum; sat.=saturated

EXAMPLES

Intermediate Ia (3R,4S)-4-Amino-2,2-difluoro-3-hydroxy-5-methyl-N-(2,2,2-trifluoroethyl)hexanamide

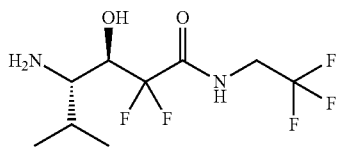 [SMILES: CC(C)[C@H](N)[C@@H](O)C(F)(F)C(=O)NCC(F)(F)F]

A] (S)-tert-Butyl (3-methyl-1-oxobutan-2-yl)carbamate

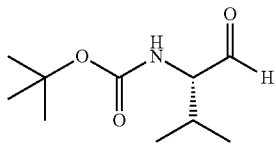

To a solution of commercially available (S)-tert-butyl (1-(methoxy(methyl)amino)-3-methyl-1-oxobutan-2-yl)carbamate (3 g, 11.5 mmol, Eq: 1) in THF (100 ml) under argon at 0° C. was added LiAlH₄ 1M in THF (11.5 ml, 11.5 mmol, Eq: 1) dropwise over 3 min (0->4° C.). After stirring for 20 min in the cold, the reaction mixture was quenched with 1N KHSO₄ solution and extracted with EtOAc; the layers were separated and the aqueous layer was back-extracted with EtOAc. The organic layers were combined, dried over Na₂SO₄ and concentrated in vacuo to yield the title compound as a colorless liquid, 2.38 g, which was used immediately for the next step.

B] Ethyl (3R,4S)-4-amino-2,2-difluoro-3-hydroxy-5-methylhexanoate

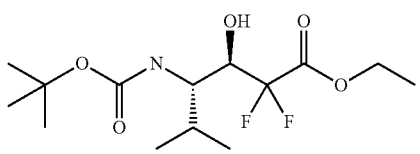 [SMILES: CCOC(=O)C(F)(F)[C@H](O)[C@@H](NC(=O)OC(C)(C)C)C(C)C]

A solution of the above prepared (S)-tert-butyl (3-methyl-1-oxobutan-2-yl)carbamate (2.01 g, 9.99 mmol, Eq: 1) and ethyl 2-bromo-2,2-difluoroacetate (6.08 g, 3.84 ml, 30 mmol, Eq: 3) in THF (15 ml) was added dropwise to a suspension of activated zinc (1.96 g, 30 mmol, Eq: 3) in THF (65 ml). Afterwards, the reaction was brought to reflux for 2 hours. The heat source was removed and the reaction was allowed to cool to ambient temperature. The reaction mixture was poured into 15 mL 1N KHSO₄ and extracted with EtOAc (2×25 mL). The organic layers were combined, washed with brine, dried over Na₂SO₄, and concentrated in vacuo. The crude material was purified by flash chromatography (silica gel, 120 g, 20% EtOAc in heptane) to deliver 1.41 g of the title compound as colorless oil.

C] tert-butyl N-[(3S,4R)-5,5-difluoro-4-hydroxy-2-methyl-6-oxo-6-(2,2,2-trifluoroethylamino)hexan-3-yl]carbamate

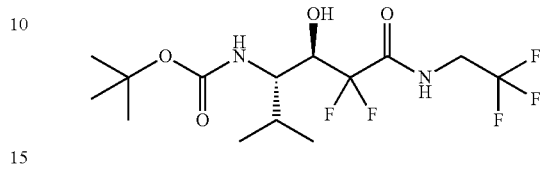

A mixture of the above prepared ethyl (3R,4S)-4-amino-2,2-difluoro-3-hydroxy-5-methylhexanoate (191.4 mg, 588 µmol, Eq: 1), 3,3,3-trifluoropropan-1-amine (333 mg, 2.94 mmol, Eq: 5) and N,N-diisopropylethylamine (380 mg, 514 µl, 2.94 mmol, Eq: 5) was refluxed in 5 mL of MeOH overnight. TLC after 17 hours showed the reaction to be finished. The reaction volume was reduced in vacuo and to the residue was added EtOAc. The organic layer was washed with brine (3×), dried over Na₂SO₄, and concentrated in vacuo. The crude material was purified by flash chromatography (silica gel, 20 g, 15% to 50% EtOAc in heptane) to produce 180 mg of the title compound as white foam; MS: 391.4(M−H)⁻.

D] (3R,4S)-4-Amino-2,2-difluoro-3-hydroxy-5-methyl-N-(2,2,2-trifluoroethyl)hexanamide

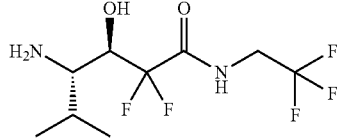 [SMILES: CC(C)[C@H](N)[C@@H](O)C(F)(F)C(=O)NCC(F)(F)F]

In a 25 mL round-bottomed flask, the above prepared tert-butyl N-[(3S,4R)-5,5-difluoro-4-hydroxy-2-methyl-6-oxo-6-(2,2,2-trifluoroethylamino)hexan-3-yl]carbamate (177 mg, 451 µmol, Eq: 1) was combined with 1,4-dioxane (6 ml) to give a colorless solution.

HCl 4M in dioxane (2.25 ml, 9 mmol, Eq: 20) was added at 0° C. and the reaction mixture was stirred overnight at rt. The crude reaction mixture was concentrated in vacuo and scrupulously dried on hv and then used directly for the next step (calculated as dihydrochloride).

Intermediate Ib (3R,4S)-4-Amino-2,2-difluoro-3-hydroxy-5-methyl-N-(2-morpholin-4-ylethyl)hexanamide

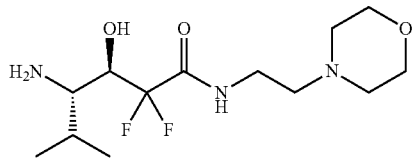 [SMILES: CC(C)[C@H](N)[C@@H](O)C(F)(F)C(=O)NCCN1CCOCC1]

Was prepared in analogy to Intermediate Ia, but using in step C] 2-morpholin-4-ylethanamine instead of 3,3,3-trifluoropropan-1-amine, as light yellow foam.

Intermediate IIa (3R,4S)-4-[[(2S)-2-Amino-2-phenylacetyl]amino]-2,2-difluoro-3-hydroxy-5-methyl-N-(2,2,2-trifluoroethyl)hexanamide

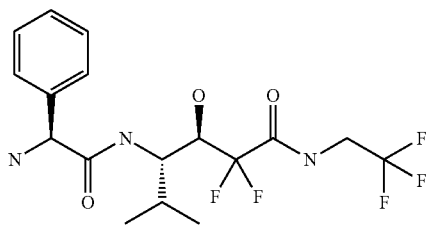 [SMILES: CC(C)[C@H](NC(=O)[C@@H](N)c1ccccc1)[C@@H](O)C(F)(F)C(=O)NCC(F)(F)F]

A] tert-Butyl N-[(1S)-2-[[(3S,4R)-5,5-difluoro-4-hydroxy-2-methyl-6-oxo-6-(2,2,2-trifluoroethylamino)hexan-3-yl]amino]-2-oxo-1-phenylethyl]carbamate

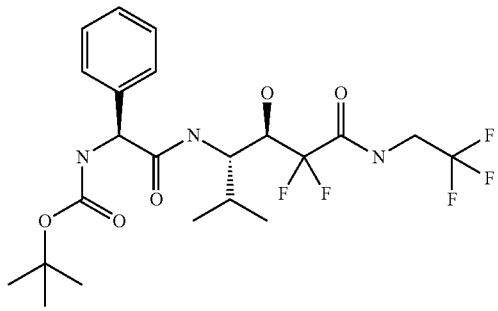 [SMILES: CC(C)[C@H](NC(=O)[C@@H](NC(=O)OC(C)(C)C)c1ccccc1)[C@@H](O)C(F)(F)C(=O)NCC(F)(F)F]

In a 25 ml flask, (3R,4S)-4-amino-2,2-difluoro-3-hydroxy-5-methyl-N-(2,2,2-trifluoroethyl)hexanamide dihydrochloride [0.3M in DMF] (Intermediate Ia, 1.33 ml, 398 µmol, Eq: 1), (S)-2-((tert-butoxycarbonyl)amino)-2-phenylacetic acid (0.100 g, 398 µmol, Eq: 1) and HATU (166 mg, 438 µmol, Eq: 1.1) were mixed in DMF (4 ml). Hunig's base (257 mg, 348 µl, 1.99 mmol, Eq: 5) was then added, and the reaction mixture was stirred at RT for 2 h. It was diluted with EtOAc, poured into 1M KHSO$_4$, and the aqueous layer was extracted with EtOAc (2×20 ml). The combined organics layers were washed with NaHCO$_3$, brine, dried over Na$_2$SO$_4$, and evaporated. Purification by flash chromatography (silica gel, 20 g, 20% to 100% EtOAc in heptane) generated 124 mg of the title compound as yellow foam; MS: 512.2 (M+H)$^-$.

B] (3R,4S)-4-[[(2S)-2-Amino-2-phenylacetyl]amino]-2,2-difluoro-3-hydroxy-5-methyl-N-(2,2,2-trifluoroethyl)hexanamide

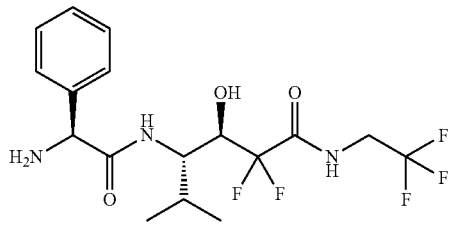 [SMILES: CC(C)[C@H](NC(=O)[C@@H](N)c1ccccc1)[C@@H](O)C(F)(F)C(=O)NCC(F)(F)F]

To a solution of the above prepared tert-butyl N-[(1S)-2-[[(3S,4R)-5,5-difluoro-4-hydroxy-2-methyl-6-oxo-6-(2,2,2-trifluoroethylamino)hexan-3-yl]amino]-2-oxo-1-phenylethyl]carbamate (0.120 g, 235 µmol, Eq: 1) in MeOH (3 ml) was added HCl 4M in dioxane (293 µl, 1.17 mmol, Eq: 5); the reaction mixture was stirred at RT for 2 hours and at 40° C. for 2 hours. LC-MS indicated the reaction to be finished. The solvent was carefully evaporated to dryness to leave 119 mg of the title compound as hydrochloride as light purple foam which was used directly for the next step; MS: 412.2 (M+H)$^+$. Instead of using MeOH, the reaction can also be performed in dioxane only.

In close analogy, using in step A] (2S)-2-(4-methoxyphenyl)-2-[(2-methylpropan-2-yl)oxycarbonylamino]acetic acid, was prepared:

Intermediate IIb (3R,4S)-4-[[(2S)-2-Amino-2-(4-methoxyphenyl)acetyl]amino]-2,2-difluoro-3-hydroxy-5-methyl-N-(2,2,2-trifluoroethyl)hexanamide

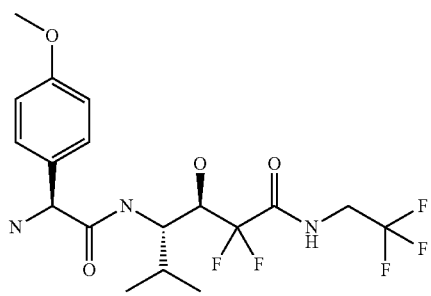 [SMILES: COc1ccc([C@H](N)C(=O)N[C@@H](C(C)C)[C@@H](O)C(F)(F)C(=O)NCC(F)(F)F)cc1]

As hydrochloride as yellow oil; MS: 442.2 (M+H)$^+$.

In close analogy, using in step A] (2S)-2-[(2-methylpropan-2-yl)oxycarbonylamino]-3-phenylpropanoic acid, was prepared:

Intermediate IIc (3R,4S)-4-[[(2S)-2-Amino-3-phenylpropanoyl]amino]-2,2-difluoro-3-hydroxy-5-methyl-N-(2,2,2-trifluoroethyl)hexanamide

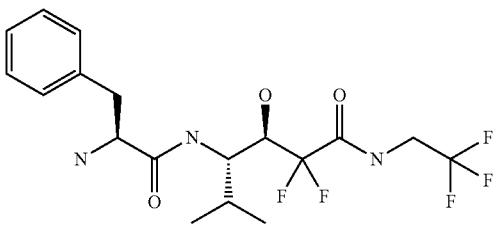 [SMILES: CC(C)[C@H](NC(=O)[C@@H](N)Cc1ccccc1)[C@@H](O)C(F)(F)C(=O)NCC(F)(F)F]

As hydrochloride as light yellow foam; MS: 426.2 (M+H)$^+$.

In close analogy, using in step A] (3R,4S)-4-amino-2,2-difluoro-3-hydroxy-5-methyl-N-(2-morpholin-4-ylethyl)hexanamide was prepared:

Intermediate IId (3R,4S)-4-[[(2S)-2-amino-2-phenylacetyl]amino]-2,2-difluoro-3-hydroxy-5-methyl-N-(2-morpholin-4-ylethyl)hexanamide

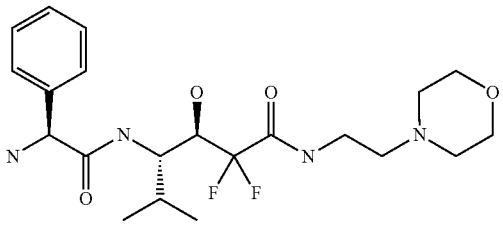 [SMILES: CC(C)[C@H](NC(=O)[C@@H](N)c1ccccc1)[C@@H](O)C(F)(F)C(=O)NCCN1CCOCC1]

As hydrochloride as light yellow foam; MS: 443.3 (M+H)$^+$.

Intermediate IIIa (2R)-2-(3,5-Dichlorophenoxy)-3-phenylpropanoic acid

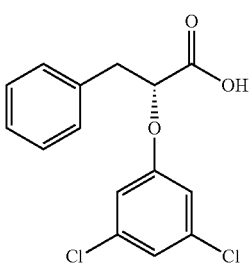 [SMILES: O=C(O)[C@@H](Cc1ccccc1)Oc1cc(Cl)cc(Cl)c1]

A] Methyl (2R)-2-(3,5-dichlorophenoxy)-3-phenylpropanoate

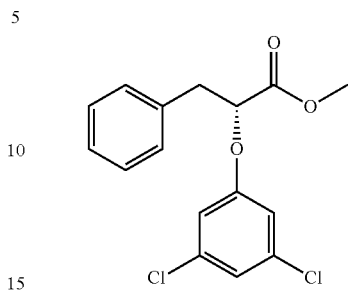

In a 50 mL pear-shaped flask, commercially available (S)-methyl 2-hydroxy-3-phenylpropanoate (500 mg, 2.77 mmol, Eq: 1) and 3,5-dichlorophenol (475 mg, 2.91 mmol, Eq: 1.05) were combined at −10 degree C. with THF (11.1 ml) to give a light brown solution; triphenylphosphine (946 mg, 3.61 mmol, Eq: 1.3) and DIAD (729 mg, 3.61 mmol, Eq: 1.3) were subsequently added and stirring continued for 1 h when TLC indicated that the starting alcohol had disappeared; the reaction mixture was quenched with 0.5 N HCl, diluted with AcOEt, the organic layers were separated, washed with cold water, dried over Na$_2$SO$_4$, and evaporated to dryness; the crude product was purified by column chromatography SiO2 (50 g, heptane/AcOEt=7/1) to yield 610 mg of the title compound as light yellow solid; MS: 323.027 (M−H)$^-$.

B] (2R)-2-(3,5-Dichlorophenoxy)-3-phenylpropanoic acid

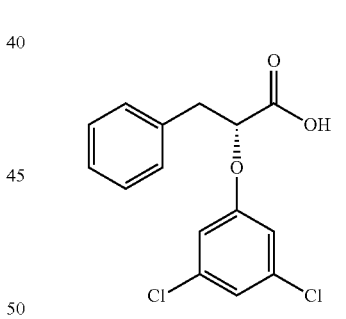

In a 50 mL pear-shaped flask, the above prepared (R)-methyl 2-(3,5-dichlorophenoxy)-3-phenylpropanoate (609 mg, 1.87 mmol, Eq: 1) was combined with THF (2.08 ml) and MeOH (2.08 mL) to give an off-white suspension; after cooling to −10 degree C., lithium hydroxide (89.7 mg, 3.75 mmol, Eq: 2) and 1.04 mL of water was added and the heterogeneous mixture stirred at the same temperature; after 3 h TLC still indicated some starting material; another 3 mL of THF was added for solubilizing, and the reaction mixture was warmed to 0 degree C.; after another 30 Min., the mixture was quenched with dil. HCl, extracted with AcOEt, the organic layers were washed with water, dried over Na$_2$SO$_4$, and evaporated to dryness; 595 mg of the title acid were thereby obtained after careful HV-drying as white crystals; MS: 309.1 (M−H)$^-$.

Intermediate IIIb (2R)-3-(3-Chlorophenyl)-2-(3,5-dichlorophenoxy)propanoic acid

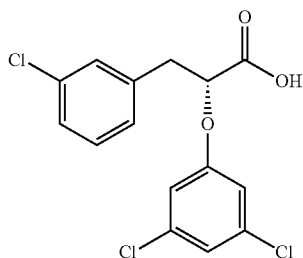 [SMILES: O=C(O)[C@@H](Cc1cccc(Cl)c1)Oc1cc(Cl)cc(Cl)c1]

A] Methyl (2S)-3-(3-chlorophenyl)-2-hydroxypropanoate

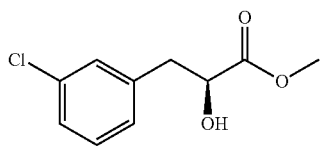

In a 100 mL four-necked flask, commercially available (S)-methyl oxirane-2-carboxylate (400 mg, 343 µl, 3.92 mmol, Eq: 1) and copper bromide dimethyl sulfide (201 mg, 980 µmol, Eq: 0.25) were combined with THF abs. (25 ml) to give a light brown suspension; after cooling to −35° C., (3-chlorophenyl)magnesium bromide (1M in THF, 7.84 ml, 7.84 mmol, Eq: 2) was slowly added via syringe within 15 Min. (slightly exothermic, temperature kept below −33° C.) and then allowed to warm to −25° C.; the reaction was quenched with sat. NH$_4$Cl sol. at −20° C., extracted with AcOEt, washed with water, dried over Na$_2$SO$_4$, and evaporated to dryness; purification by flash column chromatography (50 g SiO2, heptane/AcOEt=2/1) yielded 615 mg of the title compound as colorless oil.

B] Methyl (2R)-3-(3-chlorophenyl)-2-(3,5-dichlorophenoxy)propanoate

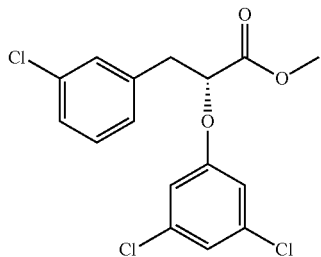 [SMILES: COC(=O)[C@@H](Cc1cccc(Cl)c1)Oc1cc(Cl)cc(Cl)c1]

In a 50 mL pear-shaped flask, the above prepared (S)-methyl 3-(3-chlorophenyl)-2-hydroxypropanoate (611 mg, 2.85 mmol, Eq: 1) and 3,5-dichlorophenol (487 mg, 2.99 mmol, Eq: 1.05) were combined at −10° C. with THF (11.4 ml) to give an off-white solution; triphenylphosphine (971 mg, 3.7 mmol, Eq: 1.3) and DIAD (748 mg, 726 µl, 3.7 mmol, Eq: 1.3) were subsequently added and stirring continued for ¾ h when TLC indicated that the starting alcohol had almost quantitatively disappeared; after 1.25 h the reaction mixture was quenched with 0.5 N HCl, diluted with AcOEt, the organic layers were separated, washed with diluted brine, dried over Na$_2$SO$_4$, and evaporated to dryness; purification by column chromatography SiO2 (50 g, heptane/AcOEt=7/1) afforded eventually 767 mg of the title product as light yellow oil.

C] (2R)-3-(3-Chlorophenyl)-2-(3,5-dichlorophenoxy)propanoic acid

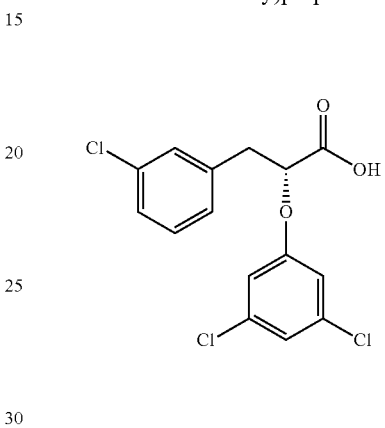

In a 75 mL pear-shaped flask, the above prepared (R)-methyl 3-(3-chlorophenyl)-2-(3,5-dichlorophenoxy)propanoate (763 mg, 2.12 mmol, Eq: 1) was combined with THF (5 ml) and MeOH (2 mL) to give an off-white solution; after cooling to 0° C., lithium hydroxide (127 mg, 5.3 mmol, Eq: 2.5) and 1 mL of water was added and the mixture stirred for 1.5 h when TLC indicated only traces, if any, of starting material to be left; after another 30 Min., the hydrolysis was quenched with dil. HCl, extracted with AcOEt, the combined organic layers washed with water, dried over Na$_2$SO$_4$, and evaporated to dryness; crystallization from heptane/AcOEt yielded 668 mg of the title acid as white crystals; MS: 343.2 (M−H)$^−$.

In close analogy to Intermediate IIIb were prepared

Intermediate IIIc (2R)-2-(3-Chloro-5-methylphenoxy)-3-(3-chlorophenyl)propanoic acid

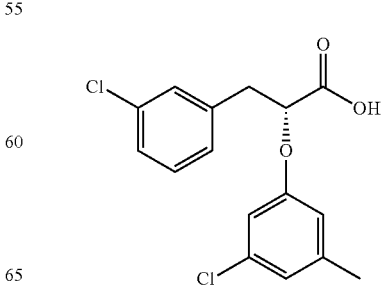

But using in step B] 3-chloro-5-methylphenol instead of 3,5-dichlorophenol, as white crystals; MS: 323.2 (M–H)⁻.

Intermediate IIId (2R)-2-(3-Chlorophenoxy)-3-(3,4-dichlorophenyl) propanoic acid

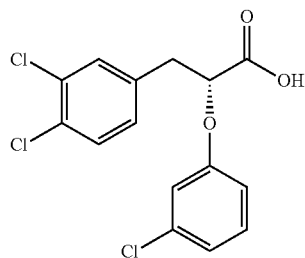 [SMILES: O=C(O)[C@@H](Cc1ccc(Cl)c(Cl)c1)Oc1cccc(Cl)c1]

But using in step A] (3,4-dichlorophenyl)magnesium bromide instead of (3-chlorophenyl)-magnesium bromide, and in step B] 3-chlorophenol instead of 3,5-dichlorophenol, as white crystals; MS: 343.1 (M–H)⁻.

Intermediate IIIe (2R)-3-(3-Chlorophenyl)-2-(3,5-dicyanophenoxy) propanoic acid

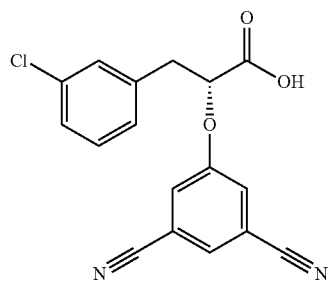 [SMILES: N#Cc1cc(C#N)cc(O[C@H](Cc2cccc(Cl)c2)C(=O)O)c1]

But using in step B] 5-hydroxybenzene-1,3-dicarbonitrile instead of 3,5-dichlorophenol, as white solid; MS: 325.2 (M–H)⁻.

Intermediate IIIf (2R)-3-(3-Chlorophenyl)-2-(5-chloropyridin-3-yl) oxypropanoic acid

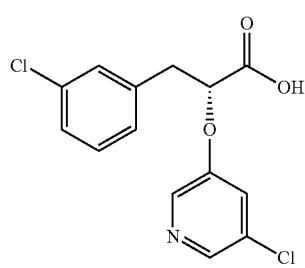

But using in step B] 5-chloropyridin-3-ol instead of 3,5-dichlorophenol, as white foam; MS: 310.2 (M–H)⁻.

Intermediate IIIg (2R)-2-(3-Chlorophenoxy)-3-(3,5-dichlorophenyl) propanoic acid

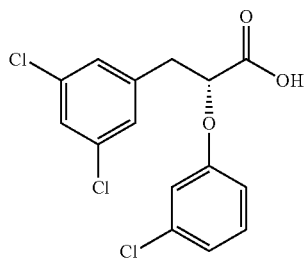 [SMILES: O=C(O)[C@@H](Cc1cc(Cl)cc(Cl)c1)Oc1cccc(Cl)c1]

But using in step A] (3,5-dichlorophenyl)magnesium bromide instead of (3-chlorophenyl)-magnesium bromide, and in step B] 3-chlorophenol instead of 3,5-dichlorophenol, as yellow semisolid; MS: 343.2 (M–H)⁻.

Intermediate IIIh (2S)-2-(3-Chlorophenoxy)-3-(3,5-dichlorophenyl) propanoic acid

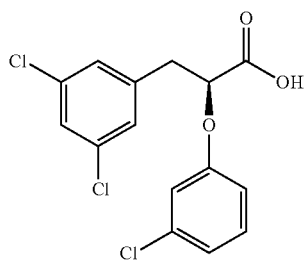 [SMILES: O=C(O)[C@H](Cc1cc(Cl)cc(Cl)c1)Oc1cccc(Cl)c1]

But using in step A] (R)-methyl oxirane-2-carboxylate instead of (S)-methyl oxirane-2-carboxylate and (3,5-dichlorophenyl)magnesium bromide instead of (3-chlorophenyl)-magnesium bromide, respectively, and in step B] 3-chlorophenol instead of 3,5-dichlorophenol, as white solid; MS: 343.2 (M–H)⁻.

Intermediate IIIi (2R)-2-(3-Chloro-5-cyanophenoxy)-3-(3-chlorophenyl)propanoic acid

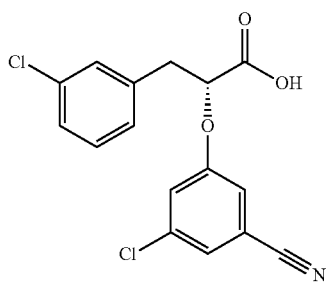 [SMILES: N#Cc1cc(Cl)cc(O[C@H](Cc2cccc(Cl)c2)C(=O)O)c1]

But using in step B] 3-chloro-5-hydroxybenzonitrile instead of 3,5-dichlorophenol, as colorless oil; MS: 334.1 (M−H)⁻.

Intermediate IIIj (rac)-2-(3-Chloro-5-cyanophenoxy)-3-(3-cyanophenyl)propanoic acid

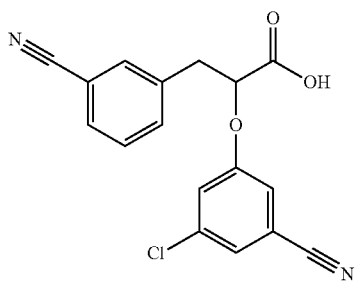 [SMILES: N#Cc1cccc(CC(Oc2cc(Cl)cc(C#N)c2)C(=O)O)c1]

A] Methyl (E,Z)-2-[tert-butyl(dimethyl)silyl]oxy-3-(3-cyanophenyl)prop-2-enoate

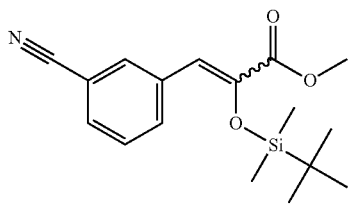 [SMILES: COC(=O)C(=Cc1cccc(C#N)c1)O[Si](C)(C)C(C)(C)C]

In a 25 mL three-necked flask, (rac)-methyl 2-((tert-butyldimethylsilyl)oxy)-2-(dimethoxyphosphoryl)-acetate (CAS Registry Number 78186-95-5, 498 mg, 1.59 mmol, Eq: 1.1) was combined with THF (10 ml) to give a colorless solution; potassium tert-butoxide (171 mg, 1.52 mmol, Eq: 1.05) was added at −10° C. and the reaction mixture was stirred for 1 hr at this temperature, then for 1 hr at 0° C. to complete deprotonation. The resultant solution was cooled down again to −10° C. and a solution of 3-formylbenzonitrile (190 mg, 1.45 mmol, Eq: 1) in THF (5 ml) was added.

The reaction was allowed to proceed for 30 min at −5° C., quenched with 10 ml sat NH₄Cl sol. and extracted with AcOEt (2×). The organic layers were washed with brine, combined, dried over Na₂SO₄ and concentrated in vacuo. Purification by flash chromatography (silica gel, 50 g, 5% to 40% EtOAc in heptane) delivered finally 381 mg of the title compound as colorless liquid (roughly 1:1 E/Z-mixture); MS: 202.1 (M-tBDMS)⁻.

B] (rac)-Methyl 2-[tert-butyl(dimethyl)silyl]oxy-3-(3-cyanophenyl)propanoate

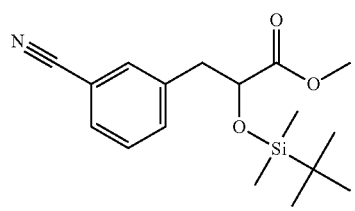 [SMILES: COC(=O)C(Cc1cccc(C#N)c1)O[Si](C)(C)C(C)(C)C]

To a solution of the above prepared (rac)-methyl 2-((tert-butyldimethylsilyl)oxy)-3-(3-cyanophenyl)-acrylate (378 mg, 1.19 mmol, Eq: 1) in EtOAc (30 ml) under argon was added Pd—C 10% (100 mg, 94 μmol, Eq: 0.079) and the mixture was stirred under an atmosphere of hydrogen at ambient temperature. TLC after 4 h showed the reaction to be finished. The mixture was filtered over a pad of Celite, washed carefully with AcOEt, and the filtrate was concentrated in vacuo. The crude material was purified by flash chromatography (silica gel, 50 g, 5% to 20% EtOAc in heptane) to deliver 192 mg of the title compound as colorless liquid; in addition, 54 mg of methyl 2-[tert-butyl(dimethyl)silyl]oxy-3-(3-methylphenyl)propanoate was isolated as byproduct.

C] (rac)-Methyl 3-(3-cyanophenyl)-2-hydroxypropanoate

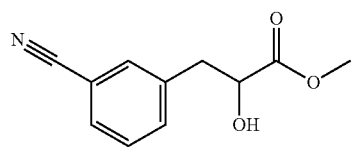

In a 10 mL round-bottomed flask, the above prepared (rac)-methyl 2-((tert-butyldimethylsilyl)-oxy)-3-(3-cyanophenyl)propanoate (186 mg, 582 μmol, Eq: 1) was combined with THF (6 ml) to give a colorless solution. TBAF 1M in THF (1.16 ml, 1.16 mmol, Eq: 2) was added at 0° C. and the yellow solution was stirred for 45 min at 0° C. when TLC showed the reaction to be finished. The reaction mixture was quenched with sat. NH₄Cl sol. and extracted with EtOAc (2×25 mL).

The organic layers were combined, dried over Na₂SO₄ and concentrated in vacuo. The crude material was purified by flash chromatography (silica gel, 20 g, 50% EtOAc in heptane) to yield 121 mg of the title alcohol as colorless liquid.

D] (rac)-Methyl 2-(3-chloro-5-cyanophenoxy)-3-(3-cyanophenyl)propanoate

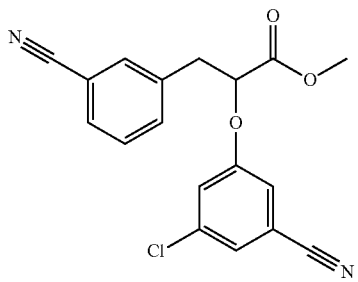 [SMILES: COC(=O)C(Cc1cccc(C#N)c1)Oc1cc(Cl)cc(C#N)c1]

To a mixture of the above prepared (rac)-methyl 3-(3-cyanophenyl)-2-hydroxypropanoate (115 mg, 560 µmol, Eq: 1) and 3-chloro-5-hydroxybenzonitrile (90.4 mg, 588 µmol, Eq: 1.05) in DCM (5 ml) were added at −10° C. triphenylphosphine (191 mg, 729 µmol, Eq: 1.3) and DIAD (147 mg, 142 µl, 729 µmol, Eq: 1.3), and the reaction allowed to proceed for 1 hr at 0° C. The mixture was quenched with sat. NH$_4$Cl and ice and extracted with DCM (2×25 mL). The organic layers were washed with brine, combined, dried over Na$_2$SO$_4$ and concentrated in vacuo. The crude material was finally purified by flash chromatography (silica gel, 20 g, 25% EtOAc in heptane) to deliver 111 mg of the title compound as colorless oil.

E] (rac)-2-(3-Chloro-5-cyanophenoxy)-3-(3-cyanophenyl)propanoic acid

In a 10 mL round-bottomed flask, the above prepared (rac)-methyl 2-(3-chloro-5-cyanophenoxy)-3-(3-cyanophenyl)propanoate (103 mg, 302 µmol, Eq: 1) was combined with THF (1 ml) and MeOH (0.5 ml) to give a colorless solution. LiOH 1M (363 µl, 363 µmol, Eq: 1.2) was added at 0° C. and the reaction mixture was stirred at the same temperature. LC-MS after 1 h showed the hydrolysis to be finished. The reaction mixture was quenched with dil. KHSO$_4$ sol. and ice, extracted with AcOEt (2×), the organic layers were washed with brine, dried (Na$_2$SO$_4$) and concentrated in vacuo to leave, after careful HV-drying, 98 mg of the title compound as white semisolid; MS: 325.2 (M−H)$^−$.

In close analogy to Intermediate IIIb were prepared

Intermediate IIIk (2R)-2-(3,5-dicyanophenoxy)-3-(3-fluorophenyl)propanoic acid

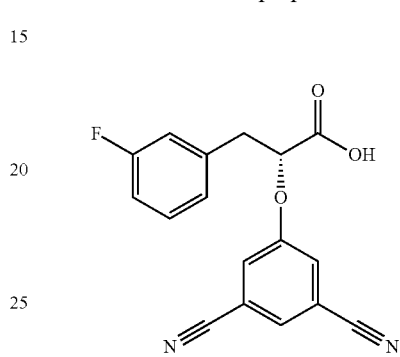

But using in step A] (3-fluorophenyl)magnesium bromide instead of (3-chlorophenyl)-magnesium bromide, and in step B] 5-hydroxyisophthalonitrile instead of 3,5-dichlorophenol, as white solid; MS: 309.1 (M−H)$^−$.

Intermediate IIIl (2R)-2-(3-cyanophenoxy)-3-(3-fluorophenyl)propanoic acid

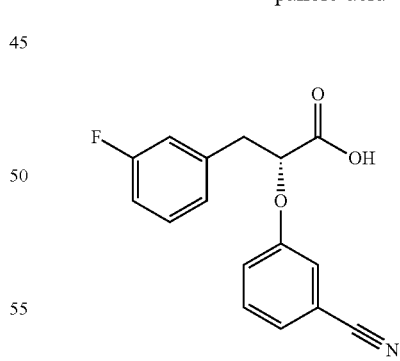

But using in step A] (3-fluorophenyl)magnesium bromide instead of (3-chlorophenyl)-magnesium bromide, and in step B] 3-hydroxybenzonitrile instead of 3,5-dichlorophenol, as white solid; MS: 284.1 (M−H)$^−$.

Intermediate IIIm (2R)-2-(3-chlorophenoxy)-3-(3-fluorophenyl)propanoic acid

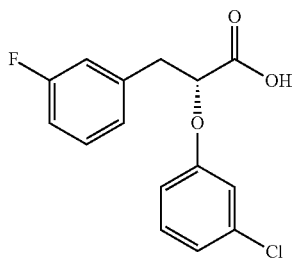 [SMILES: O=C(O)[C@@H](Cc1cccc(F)c1)Oc1cccc(Cl)c1]

But using in step A] (3-fluorophenyl)magnesium bromide instead of (3-chlorophenyl)-magnesium bromide, and in step B] 3-chlorophenol instead of 3,5-dichlorophenol, as white solid; MS: 293.1 (M–H)$^-$.

Example 1

(4S)-4-[[(2S)-2-[[(2R)-2-(3,5-Dichlorophenoxy)-3-phenylpropanoyl]amino]-3-phenylpropanoyl]amino]-2,2-difluoro-5-methyl-3-oxo-N-(2,2,2-trifluoroethyl)hexanamide

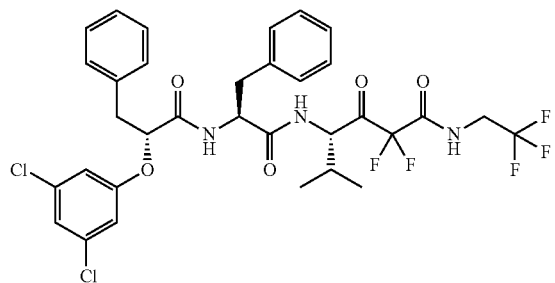 [SMILES: CC(C)[C@H](NC(=O)[C@H](Cc1ccccc1)NC(=O)[C@@H](Cc1ccccc1)Oc1cc(Cl)cc(Cl)c1)C(=O)C(F)(F)C(=O)NCC(F)(F)F]

A] (3R,4S)-4-[[(2S)-2-[[(2R)-2-(3,5-Dichlorophenoxy)-3-phenylpropanoyl]amino]-3-phenylpropanoyl]amino]-2,2-difluoro-3-hydroxy-5-methyl-N-(2,2,2-trifluoroethyl)hexanamide

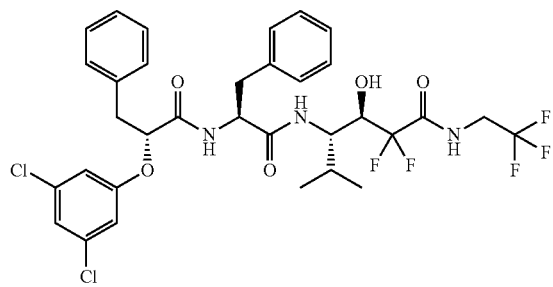 [SMILES: CC(C)[C@H](NC(=O)[C@H](Cc1ccccc1)NC(=O)[C@@H](Cc1ccccc1)Oc1cc(Cl)cc(Cl)c1)C(=O)C(F)(F)C(=O)NCC(F)(F)F]

In a 10 mL round-bottomed flask, (R)-2-(3,5-dichlorophenoxy)-3-phenylpropanoic acid (Intermediate IIIa, 50 mg, 161 μmol, Eq: 1) and Hunig's base (104 mg, 140 μl, 803 μmol, Eq: 5) were combined with DMF (4 ml) to give a colorless solution; (4S)-4-((S)-2-amino-3-phenylpropanamido)-2,2-difluoro-3-hydroxy-5-methyl-N-(2,2,2-trifluoroethyl)hexanamide hydrochloride (Intermediate IIc, 74.2 mg, 161 μmol, Eq: 1) and HATU (73.3 mg, 193 μmol, Eq: 1.2) were added at 0° C. (–>yellow solution) and the reaction mixture was stirred at rt for 3 h. The reaction mixture was then poured into sat. NaHCO$_3$ sol. and extracted with EtOAc (2×). The organic layers were washed with 1N KHSO$_4$ and brine, combined, dried over Na$_2$SO$_4$ and evaporated in vacuo. The crude material was purified by flash chromatography (silica gel, 20 g, 10% to 60% EtOAc in heptane) to yield 67 mg of the title compound as white foam; 718.2 (M+H)$^+$.

B] (4S)-4-[[(2S)-2-[[(2R)-2-(3,5-Dichlorophenoxy)-3-phenylpropanoyl]amino]-3-phenylpropanoyl]amino]-2,2-difluoro-5-methyl-3-oxo-N-(2,2,2-trifluoroethyl)hexanamide

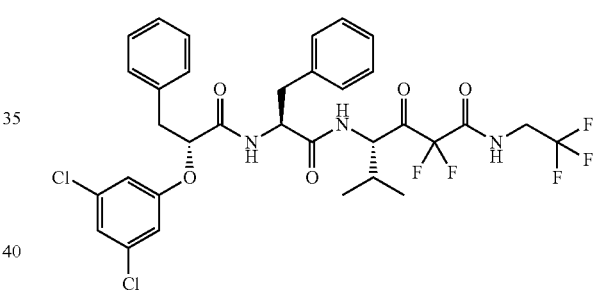

In a 10 mL round-bottomed flask, the above prepared (4S)-4-((S)-2-((R)-2-(3,5-dichlorophenoxy)-3-phenylpropanamido)-3-phenylpropanamido)-2,2-difluoro-3-hydroxy-5-methyl-N-(2,2,2-trifluoroethyl)hexanamide (63.4 mg, 88.2 μmol, Eq: 1) was combined with DCM (4 ml) to give a colorless solution. Dess-Martin periodinane 15% in dichloromethane (374 mg, 275 μl, 132 μmol, Eq: 1.5) was added at 0° C. and the reaction mixture was stirred at rt for 2 h when TLC indicated the reaction to be finished. The reaction mixture was poured into sat. NaHCO$_3$ sol. and extracted with DCM (2×). The organic layers were washed with brine, combined, dried over Na$_2$SO$_4$ and concentrated in vacuo. The crude material was purified by flash chromatography (silica gel, 10 g, 33.3% EtOAc in heptane) to afford 38.5 mg of the title product as white solid; MS: 716.2 (M+H)$^+$.

In close analogy to example 1 were prepared, using the appropriate intermediates as indicated in the following Table:

| Ex | Name | Structure | Intermediates | Form, Color, MS |
|---|---|---|---|---|
| 2 | N-[(2S)-3-(3,4-Dichlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyridine-2-carboxamide | 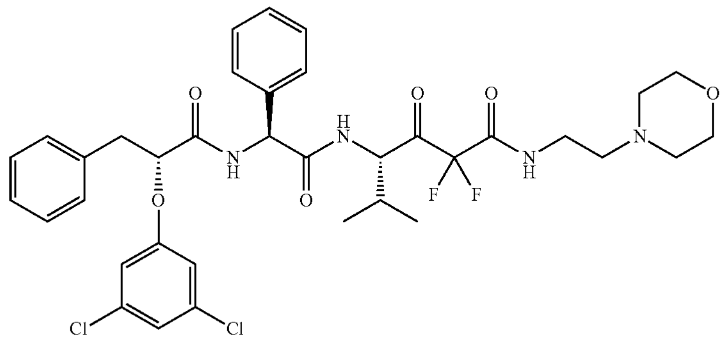 | IId IIIa | solid, white, 730.3 (M + H)+ |
| 3 | (4S)-4-[[(2S)-2-[[(2R)-2-(3,5-dichlorophenoxy)-3-phenylpropanoyl]amino]-2-(4-methoxyphenyl)acetyl]amino]-2,2-difluoro-5-methyl-3-oxo-N-(2,2,2-trifluoroethyl)hexanamide | 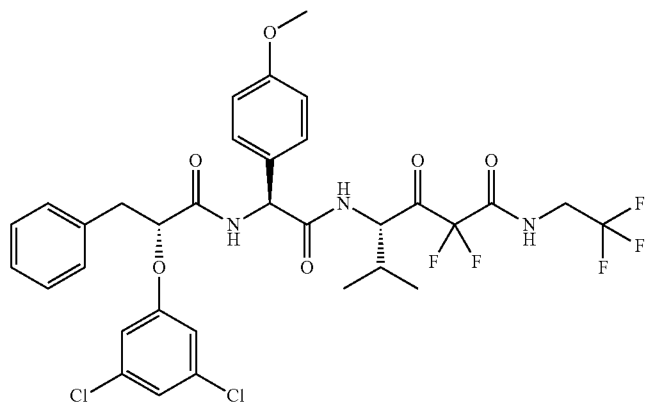 [SMILES: COc1ccc([C@H](NC(=O)[C@@H](Cc2ccccc2)Oc2cc(Cl)cc(Cl)c2)C(=O)N[C@H](C(=O)C(F)(F)C(=O)NCC(F)(F)F)C(C)C)cc1] | IIb IIIa | solid, white, 732.4 (M + H)+ |
| 4 | (4S)-4-[[(2S)-2-[[(2R)-3-(3-chlorophenyl)-2-(3,5-dichlorophenoxy)propanoyl]amino]-2-(4-methoxyphenyl)acetyl]amino]-2,2-difluoro-5-methyl-3-oxo-N-(2,2,2-trifluoroethyl)hexanamide | 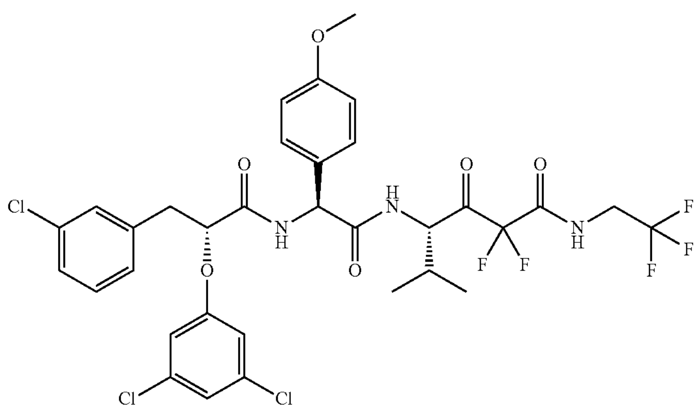 [SMILES: COc1ccc([C@H](NC(=O)[C@@H](Cc2cccc(Cl)c2)Oc2cc(Cl)cc(Cl)c2)C(=O)N[C@H](C(=O)C(F)(F)C(=O)NCC(F)(F)F)C(C)C)cc1] | IIb IIIb | solid, white, 766.3 (M + H)+ |
| 5 | (4S)-4-[[(2S)-2-[[(2R)-2-(3-chloro-5-methylphenoxy)-3-(3-chlorophenyl)propanoyl]amino]-2-(4-methoxyphenyl)acetyl]amino]-2,2-difluoro-5-methyl-3-oxo-N-(2,2,2-trifluoroethyl)hexanamide | 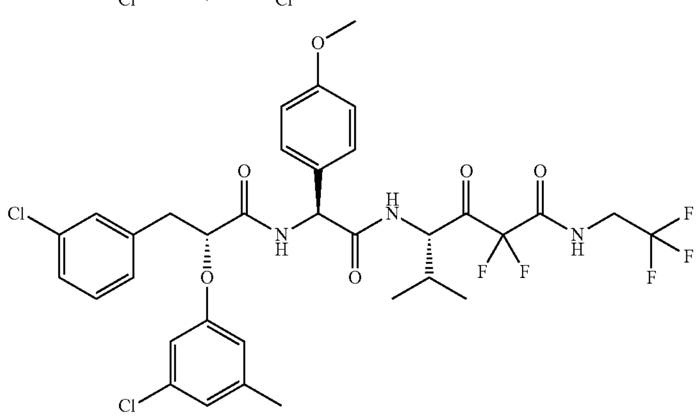 | IIb IIIc | solid, white, 746.4 (M + H)+ |

| Ex | Name | Structure | Intermediates | Form, Color, MS |
|---|---|---|---|---|
| 6 | (4S)-4-[[(2S)-2-[[(2R)-2-(3-chlorophenoxy)-3-(3,4-dichlorophenyl)propanoyl]amino]-2-(4-methoxyphenyl)acetyl]amino]-2,2-difluoro-5-methyl-3-oxo-N-(2,2,2-trifluoroethyl)hexanamide | 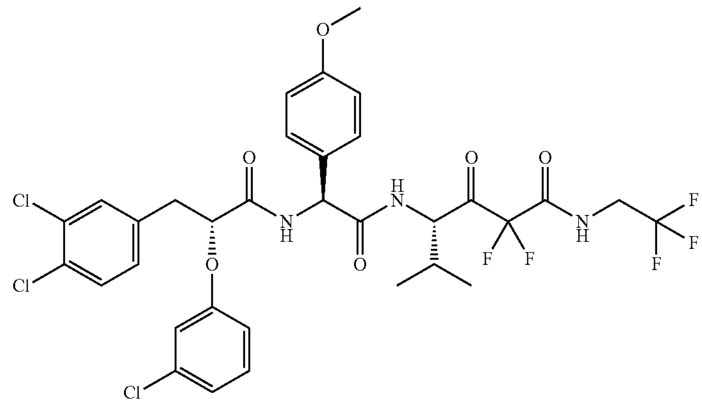 [SMILES: COc1ccc([C@H](NC(=O)[C@@H](Cc2ccc(Cl)c(Cl)c2)Oc2cccc(Cl)c2)C(=O)N[C@H](C(=O)C(F)(F)C(=O)NCC(F)(F)F)C(C)C)cc1] | IIb IIId | solid, white, 768.4 (M + H)+ |
| 7 | (4S)-4-[[(2S)-2-[[(2R)-3-(3-chlorophenyl)-2-(3,5-dicyanophenoxy)propanoyl]amino]-2-(4-methoxyphenyl)acetyl]amino]-2,2-difluoro-5-methyl-3-oxo-N-(2,2,2-trifluoroethyl)hexanamide | 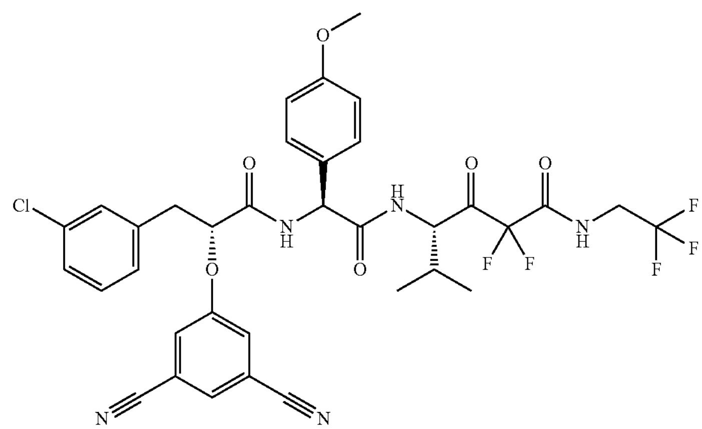 [SMILES: COc1ccc([C@H](NC(=O)[C@@H](Cc2cccc(Cl)c2)Oc2cc(C#N)cc(C#N)c2)C(=O)N[C@H](C(=O)C(F)(F)C(=O)NCC(F)(F)F)C(C)C)cc1] | IIb IIIe | solid, white, 748.4 (M + H)+ |
| 8 | (4S)-4-[[(2S)-2-[[(2R)-3-(3-chlorophenyl)-2-(5-chloropyridin-3-yl)oxypropanoyl]amino]-2-(4-methoxyphenyl)acetyl]amino]-2,2-difluoro-5-methyl-3-oxo-N-(2,2,2-trifluoroethyl)hexanamide | 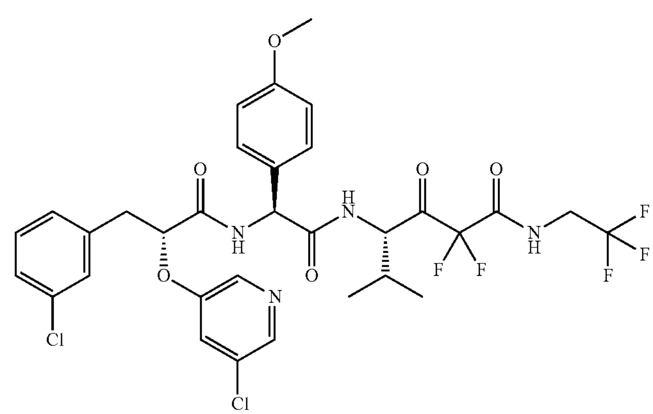 [SMILES: COc1ccc([C@H](NC(=O)[C@@H](Cc2cccc(Cl)c2)Oc2cncc(Cl)c2)C(=O)N[C@H](C(=O)C(F)(F)C(=O)NCC(F)(F)F)C(C)C)cc1] | IIb IIIf | solid, white, 733.4 (M + H)+ |

| Ex | Name | Structure | Intermediates | Form, Color, MS |
|----|------|-----------|---------------|-----------------|
| 9 | (4S)-4-[[(2S)-2-[[(2R)-2-(3-chlorophenoxy)-3-(3,5-dichlorophenyl)propanoyl]amino]-2-(4-methoxyphenyl)acetyl]amino]-2,2-difluoro-5-methyl-3-oxo-N-(2,2,2-trifluoroethyl)hexanamide | 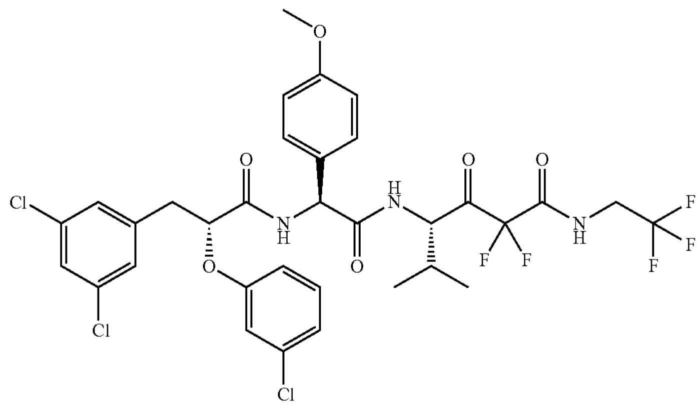 [SMILES: COc1ccc([C@H](NC(=O)[C@@H](Cc2cc(Cl)cc(Cl)c2)Oc2cccc(Cl)c2)C(=O)N[C@H](C(=O)C(F)(F)C(=O)NCC(F)(F)F)C(C)C)cc1] | IIb IIIg | solid, white, 766.5 (M − H)− |
| 10 | (4S)-4-[[(2S)-2-[[(2S)-3-(3-chlorophenyl)-2-(3,5-dichlorophenoxy)propanoyl]amino]-2-(4-methoxyphenyl)acetyl]amino]-2,2-difluoro-5-methyl-3-oxo-N-(2,2,2-trifluoroethyl)hexanamide | 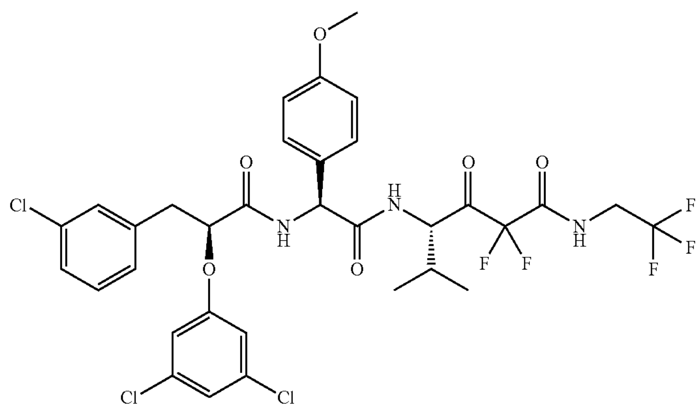 [SMILES: COc1ccc([C@H](NC(=O)[C@H](Cc2cccc(Cl)c2)Oc2cc(Cl)cc(Cl)c2)C(=O)N[C@H](C(=O)C(F)(F)C(=O)NCC(F)(F)F)C(C)C)cc1] | IIb IIIh | solid, white, 768.3 (M + H) |
| 11 | (4S)-4-[[(2S)-2-[[(2S)-3-(3-chlorophenyl)-2-(3,5-dichlorophenoxy)propanoyl]amino]-2-phenylacetyl]amino]-2,2-difluoro-5-methyl-3-oxo-N-(2,2,2-trifluoroethyl)hexanamide | 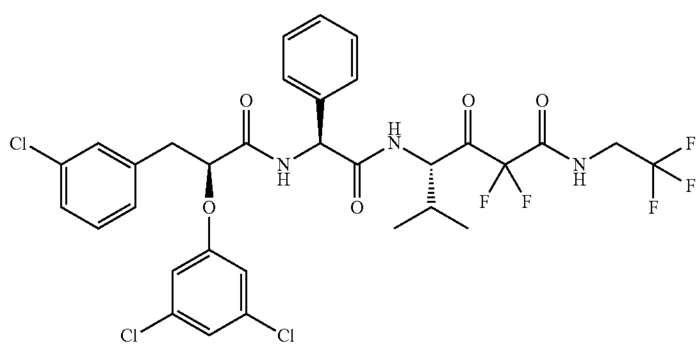 [SMILES: CC(C)[C@H](NC(=O)[C@@H](NC(=O)[C@H](Cc1cccc(Cl)c1)Oc1cc(Cl)cc(Cl)c1)c1ccccc1)C(=O)C(F)(F)C(=O)NCC(F)(F)F] | IIa IIIh | solid, white, 738.3 (M + H) |
| 12 | (4S)-4-[[(2S)-2-[[(2R)-2-(3-chloro-5-cyanophenoxy)-3-(3-chlorophenyl)propanoyl]amino]-2-(4-methoxyphenyl)acetyl]amino]-2,2-difluoro-5-methyl-3-oxo-N-(2,2,2-trifluoroethyl)hexanamide | 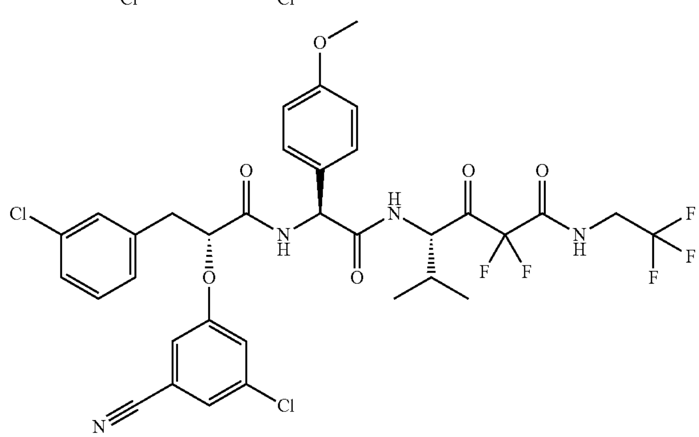 | IIb IIIi | solid, white, 757.3 (M + H) |

| Ex | Name | Structure | Intermediates | Form, Color, MS |
|---|---|---|---|---|
| 13 | (4S)-4-[[(2S)-2-[[(2R)-2-(3-chloro-5-cyanophenoxy)-3-(3-chlorophenyl)propanoyl]amino]-2-phenylacetyl]amino]-2,2-difluoro-5-methyl-3-oxo-N-(2,2,2-trifluoroethyl)hexanamide | 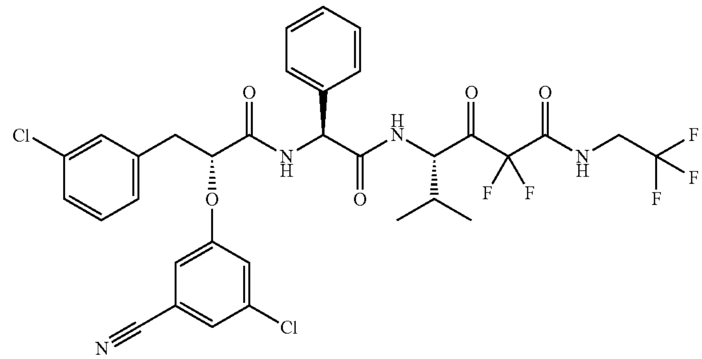 [SMILES: CC(C)[C@H](NC(=O)[C@@H](NC(=O)[C@@H](Cc1cccc(Cl)c1)Oc1cc(Cl)cc(C#N)c1)c1ccccc1)C(=O)C(F)(F)C(=O)NCC(F)(F)F] | IIa IIIi | solid, white, 727.3 (M + H) |
| 14 | (4S)-4-[[(2S)-2-[[(2R)-2-(3-chloro-5-cyanophenoxy)-3-(3-chlorophenyl)propanoyl]amino]-2-phenylacetyl]amino]-2,2-difluoro-5-methyl-3-oxo-N-(2,2,2-trifluoroethyl)hexanamide | 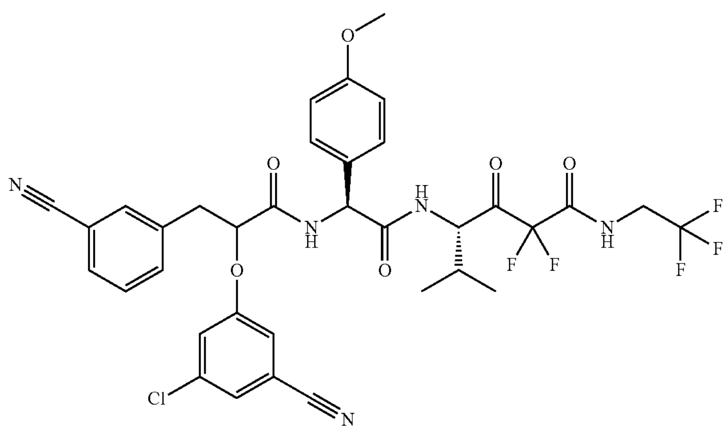 [SMILES: COc1ccc([C@H](NC(=O)C(Cc2cccc(C#N)c2)Oc2cc(Cl)cc(C#N)c2)C(=O)N[C@H](C(=O)C(F)(F)C(=O)NCC(F)(F)F)C(C)C)cc1] | IIb IIIj | semisolid, white, 748.3 (M + H) |
| 15 | (4S)-4-[[(2S)-2-[[(2R)-2-(3-dicyanophenoxy)-3-(3-fluorophenyl)propanoyl]amino]-2-(4-methoxyphenyl)acetyl]amino]-2,2-difluoro-5-methyl-3-oxo-N-(2,2,2-trifluoroethyl)hexanamide | 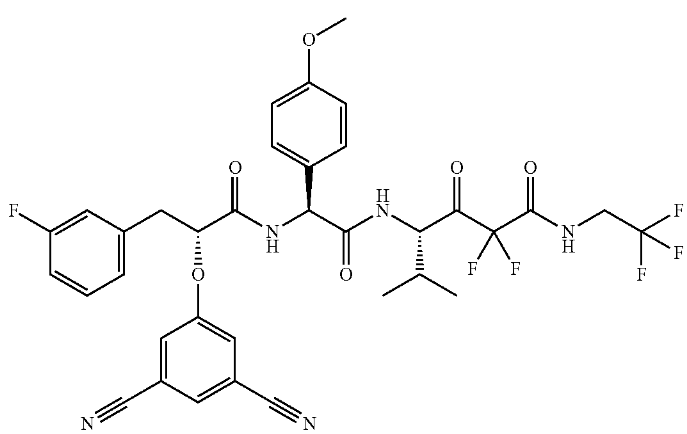 [SMILES: COc1ccc([C@H](NC(=O)[C@@H](Cc2cccc(F)c2)Oc2cc(C#N)cc(C#N)c2)C(=O)N[C@H](C(=O)C(F)(F)C(=O)NCC(F)(F)F)C(C)C)cc1] | IIb IIIk | solid, white, 732.2 (M + H) |

| Ex | Name | Structure | Intermediates | Form, Color, MS |
|---|---|---|---|---|
| 16 | (4S)-4-[[(2S)-2-[[(2R)-2-(3-cyanophenoxy)-3-(3-fluorophenyl)propanoyl]amino]-2-(4-methoxyphenyl)acetyl]amino]-2,2-difluoro-5-methyl-3-oxo-N-(2,2,2-trifluoroethyl)hexanamide | 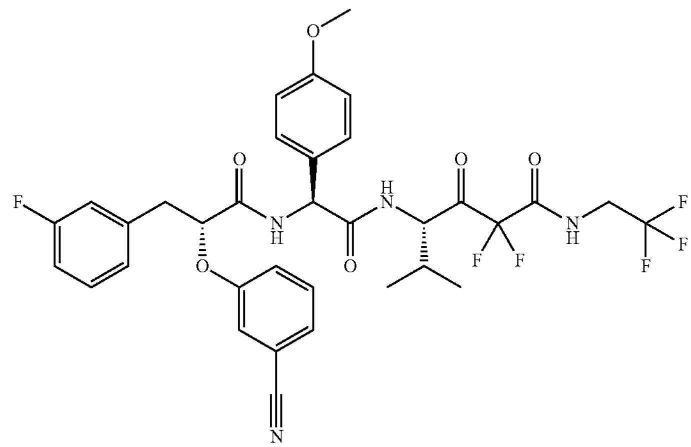 [SMILES: COc1ccc([C@H](NC(=O)[C@@H](Cc2cccc(F)c2)Oc2cccc(C#N)c2)C(=O)N[C@H](C(=O)C(F)(F)C(=O)NCC(F)(F)F)C(C)C)cc1] | IIb IIIl | solid, white, 707.2 (M + H) |
| 17 | (4S)-4-[[(2S)-2-[[(2R)-2-(3-chlorophenoxy)-3-(3-fluorophenyl)propanoyl]amino]-2-(4-methoxyphenyl)acetyl]amino]-2,2-difluoro-5-methyl-3-oxo-N-(2,2,2-trifluoroethyl)hexanamide | 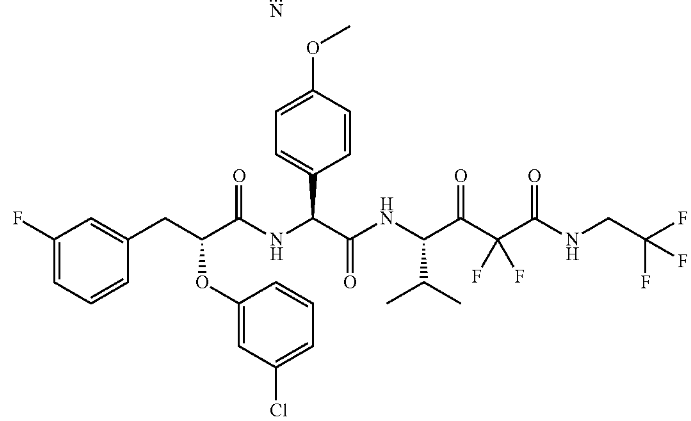 | IIb IIIm | solid, white, 716.2 (M + H) |

Example A

A compound of formula (I) can be used in a manner known per se as the active ingredient for the production of tablets of the following composition:

Per tablet

Active ingredient 200 mg

Microcrystalline cellulose 155 mg

Corn starch 25 mg

Talc 25 mg

Hydroxypropylmethylcellulose 20 mg

Total amount 425 mg

Example B

A compound of formula (I) can be used in a manner known per se as the active ingredient for the production of capsules of the following composition:

Per capsule

| Active ingredient | 100.0 mg |
|---|---|
| Corn starch | 20.0 mg |
| Lactose | 95.0 mg |
| Talc | 4.5 mg |
| Magnesium stearate | 0.5 mg |
| Total amount | 220.0 mg |

The invention claimed is:

1. A compound of formula (I)

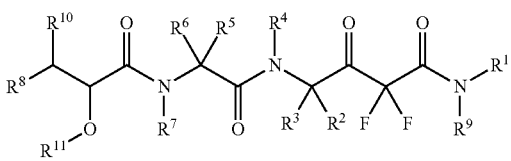

or a pharmaceutically acceptable salt thereof, wherein
$R^1$ is selected from
 i) $C_{1-6}$-alkyl,
 ii) $C_{3-8}$-cycloalkyl substituted with $R^{24}$, $R^{25}$ and $R^{26}$,
 iii) halo-$C_{1-6}$-alkyl,
 iv) heterocycloalkyl-$C_{1-6}$-alkyl substituted with $R^{24}$, $R^{25}$ and $R^{26}$,
 v) aryl-$C_{1-6}$-alkyl substituted with $R^{24}$, $R^{25}$ and $R^{26}$, and vi) heteroaryl-$C_{1-6}$-alkyl substituted with $R^{24}$, $R^{25}$ and $R^{26}$;

$R^2$, $R^3$, $R^4$, $R^6$, $R^7$, $R^9$ and $R^{10}$ are independently selected from
i) H,
ii) $C_{1-6}$-alkyl, and
iii) $C_{3-8}$-cycloalkyl;

$R^5$ is selected from
i) aryl substituted with $R^{12}$, $R^{13}$ and $R^{14}$,
ii) aryl-$C_{1-6}$-alkyl substituted with $R^{12}$, $R^{13}$ and $R^{14}$,
iii) heteroaryl substituted with $R^{12}$, $R^{13}$ and $R^{14}$, and
iv) heteroaryl-$C_{1-6}$-alkyl substituted with $R^{12}$, $R^{13}$ and $R^{14}$, $R^8$ is selected from
i) H,
ii) hydroxy,
iii) amino-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
iv) aminocarbonyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
v) aminocarbonyl-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
vi) carboxy,
vii) carboxy-$C_{1-6}$-alkyl,
viii) $C_{1-6}$-alkoxy,
ix) $C_{1-6}$-haloalkoxy,
x) $C_{1-6}$-alkoxycarbonyl,
xi) $C_{1-6}$-alkoxycarbonyl-$C_{1-6}$-alkyl,
xii) $C_{3-8}$-cycloalkyl,
xiii) aryl substituted with $R^{15}$, $R^{16}$ and $R^{17}$,
xiv) aryl-$C_{1-6}$-alkyl substituted with $R^{15}$, $R^{16}$ and $R^{17}$,
xv) aryl-$C_{1-6}$-alkoxy substituted with $R^{15}$, $R^{16}$ and $R^{17}$,
xvi) heteroaryl substituted with $R^{15}$, $R^{16}$ and $R^{17}$,
xvii) heteroaryl-$C_{1-6}$-alkyl substituted with $R^{15}$, $R^{16}$ and $R^{17}$, end
xviii) heteroaryl-$C_{1-6}$-alkoxy substituted with $R^{15}$, $R^{16}$ and $R^{17}$
xix) heterocycloalkyl substituted with $R^{15}$, $R^{16}$ and $R^{17}$,
xx) heterocycloalkyl —$C_{1-6}$-alkyl substituted with $R^{15}$, $R^{16}$ and $R^{17}$, and
xxi) heterocycloalkyl —$C_{1-6}$-alkoxy substituted with $R^{15}$, $R^{16}$ and $R^{17}$;

$R^{11}$ is selected from
i) amino-$C_{1-6}$-alkyl substituted on the nitrogen atom by $R^{21}$ and $R^{22}$,
ii) $C_{3-8}$-cycloalkyl substituted with $R^{18}$, $R^{19}$ and $R^{20}$,
iii) $C_{3-8}$-cycloalkyl-$C_{1-6}$-alkyl substituted with $R^{18}$, $R^{19}$ and $R^{20}$,
iv) $C_{3-8}$-cycloalkyl(halo)-$C_{1-6}$-alkyl substituted with $R^{18}$, $R^{19}$ and $R^{20}$,
v) aryl substituted with $R^{18}$, $R^{19}$ and $R^{20}$,
vi) aryl-$C_{1-6}$-alkyl substituted with $R^{18}$, $R^{19}$ and $R^{20}$,
vii) aryl-$C_{3-9}$-cycloalkyl substituted with $R^{18}$, $R^{19}$ and $R^{20}$,
viii) aryl-heterocycloalkyl substituted with $R^{18}$, $R^{19}$ and $R^{20}$,
ix) aryl(halo)-$C_{1-6}$-alkyl substituted with $R^{18}$, $R^{19}$ and $R^{20}$,
x) aryl(halo)-$C_{3-8}$-cycloalkyl substituted with $R^{18}$, $R^{19}$ and $R^{20}$,
xi) aryl(halo)-heterocycloalkyl substituted with $R^{18}$, $R^{19}$ and $R^{20}$,
xii) aryloxy-$C_{1-6}$-alkyl substituted with $R^{18}$, $R^{19}$ and $R^{20}$,
xiii) aryloxy-$C_{3-8}$-cycloalkyl substituted with $R^{18}$, $R^{19}$ and $R^{20}$,
xiv) aryloxy-heterocycloalkyl substituted with $R^{18}$, $R^{19}$ and $R^{20}$,
xv) aryloxy(halo)-$C_{3-8}$-cycloalkyl substituted with $R^{18}$, $R^{19}$ and $R^{20}$,
xvi) aryloxy(halo)-heterocycloalkyl substituted with $R^{18}$, $R^{19}$ and $R^{20}$,
xvii) aryloxy(halo)-$C_{1-6}$-alkyl,
xviii) heterocycloalkyl substituted with $R^{18}$, $R^{19}$ and $R^{20}$,
xix) heterocycloalkyl-$C_{1-6}$-alkyl substituted with $R^{18}$, $R^{19}$ and $R^{20}$,
xx) heterocycloalkyl-$C_{3-8}$-cycloalkyl substituted with $R^{18}$, $R^{19}$ and $R^{20}$,
xxi) heterocycloalkyl(halo)-$C_{3-8}$-cycloalkyl substituted with $R^{18}$, $R^{19}$ and $R^{20}$,
xxii) heterocycloalkyl(halo)-$C_{1-6}$-alkyl substituted with $R^{18}$, $R^{19}$ and $R^{20}$,
xxiii) heteroaryl substituted with $R^{18}$, $R^{19}$ and $R^{20}$,
xxiv) heteroaryl-$C_{1-6}$-alkyl substituted with $R^{18}$, $R^{19}$ and $R^{20}$,
xxv) heteroaryl-$C_{3-8}$-cycloalkyl substituted with $R^{18}$, $R^{19}$ and $R^{20}$,
xxvi) heteroaryl(halo)-$C_{3-8}$-cycloalkyl substituted with $R^{18}$, $R^{19}$ and $R^{20}$,
xxvii) heteroaryl(halo)-$C_{1-6}$alkyl substituted with $R^{18}$, $R^{19}$ and $R^{20}$,
xxviii) heteroaryloxy-$C_{1-6}$-alkyl substituted with $R^{18}$, $R^{19}$ and $R^{20}$,
xxix) heteroaryloxy-$C_{3-8}$-cycloalkyl substituted with $R^{18}$, $R^{19}$ and $R^{20}$,
xxx) heteroaryloxy(halo)-$C_{3-8}$-cycloalkyl substituted with $R^{18}$, $R^{19}$ and $R^{20}$, and
xxxi) heteroaryloxy(halo)-$C_{1-6}$-alkyl substituted with $R^{18}$, $R^{19}$ and $R^{20}$;

$R^{12}$, $R^{13}$, $R^{14}$, $R^{15}$, $R^{16}$, $R^{17}$, $R^{18}$, $R^{19}$, $R^{20}$, $R^{24}$, $R^{25}$ and $R^{26}$ are independently selected from
i) H,
ii) cyano,
iii) halogen,
iv) oxo,
v) $C_{1-6}$-alkyl,
vi) amino substituted on the nitrogen atom by two substituents independently selected from H, $C_{1-6}$-alkyl, $C_{1-6}$-alkoxycarbonyl, arylcarbonyl and heteroarylcarbonyl,
vii) amino-$C_{1-6}$-alkyl substituted on the nitrogen atom by two substituents independently selected from H, $C_{1-6}$-alkyl, $C_{1-6}$-alkoxycarbonyl, arylcarbonyl and heteroarylcarbonyl,
viii) $C_{1-6}$-alkyl,
ix) halo-$C_{1-6}$-alkyl,
x) $C_{3-8}$-cycloalkyl,
xi) $C_{1-6}$-alkoxycarbonyl-$C_{1-6}$-alkyl,
xii) carboxy-$C_{1-6}$-alkyl,
xiii) $C_{1-6}$-alkoxycarbonyl-$C_{1-6}$-alkylaminocarbonyl-$C_{1-6}$alkyl,
xiv) carboxy-$C_{1-6}$-alkylaminocarbonyl-$C_{1-6}$alkyl,
xv) $C_{1-6}$-alkoxy,
xvi) halo-$C_{1-6}$-alkoxy, xvii) $C_{1-6}$-alkoxycarbonyl-$C_{1-6}$-alkoxy,
xviii) carboxy-$C_{1-6}$-alkoxy,
xix) $C_{1-6}$alkoxycarbonyl-$C_{1-6}$alkylaminocarbonyl-$C_{1-6}$alkoxy,
xx) carboxy-$C_{1-6}$alkylaminocarbonyl-$C_{1-6}$alkoxy,
xxi) heterocycloalkyl,
and
$R^{21}$ and $R^{22}$ are independently selected from
i) H,
ii) $C_{1-6}$-alkoxycarbonyl,
iii) carboxy-$C_{1-6}$-alkyl,
iv) arylcarbonyl, and
v) heteroarylcarbonyl.

2. The compound of claim 1, or a pharmaceutically acceptable salt thereof, wherein
$R^1$ is selected from
i) halo-$C_{1-6}$-alkyl, and
ii) heterocycloalkyl-$C_{1-6}$-alkyl substituted with $R^{24}$, $R^{25}$ and $R^{26}$;
$R^2$ is $C_{1-6}$-alkyl;
$R^3$, $R^4$, $R^6$, $R^7$, $R^9$ and $R^{10}$ are each H;
$R^5$ is selected from
i) phenyl substituted with $R^{12}$, $R^{13}$ and $R^{14}$, and
ii) phenyl-$C_{1-6}$-alkyl substituted with $R^{12}$, $R^{13}$ and $R^{14}$;
$R^8$ is phenyl substituted with $R^{15}$, $R^{16}$ and $R^{17}$;
$R^{11}$ is selected from
i) phenyl substituted with $R^{18}$, $R^{19}$ and $R^{20}$, and
ii) pyridinyl substituted with $R^{18}$, $R^{19}$ and $R^{20}$;
$R^{12}$ is selected from
i) H, and
ii) $C_{1-6}$-alkoxy;
$R^{13}$, $R^{14}$, $R^{17}$, $R^{20}$, $R^{24}$, $R^{25}$ and $R^{26}$ are each H;
$R^{15}$ is selected from
i) H,
ii) cyano, and
iii) halogen;
$R^{16}$ is selected from
i) H, and
ii) halogen;
$R^{18}$ is selected from
i) halogen, and
ii) cyano;
and
$R^{19}$ is selected from
i) H,
ii) cyano,
iii) $C_{1-6}$-alkyl, and
iv) halogen.

3. The compound of claim 1, or a pharmaceutically acceptable salt thereof, wherein $R^1$ is selected from
i) halo-$C_{1-6}$-alkyl, and
ii) heterocycloalkyl-$C_{1-6}$-alkyl substituted with $R^{24}$, $R^{25}$ and $R^{26}$.

4. The compound of claim 1, or a pharmaceutically acceptable salt thereof, wherein $R^1$ is halo-$C_{1-6}$-alkyl.

5. The compound of claim 1, or a pharmaceutically acceptable salt thereof, wherein $R^1$ is trifluoroethyl.

6. The compound of claim 1, or a pharmaceutically acceptable salt thereof, wherein $R^2$ is $C_{1-6}$-alkyl.

7. The compound of claim 1, or a pharmaceutically acceptable salt thereof, wherein $R^2$ is isopropyl.

8. The compound of claim 1, or a pharmaceutically acceptable salt thereof, wherein $R^3$, $R^4$, $R^6$, $R^7$, $R^9$ and $R^{10}$ are H.

9. The compound of claim 1, or a pharmaceutically acceptable salt thereof, wherein $R^5$ is elected from
i) phenyl substituted with $R^{12}$, $R^{13}$ and $R^{14}$, and
ii) phenyl-$C_{1-6}$-alkyl substituted with $R^{12}$, $R^{13}$ and $R^{14}$.

10. The compound of claim 1, or a pharmaceutically acceptable salt thereof, wherein $R^5$ is phenyl substituted with $R^{12}$, $R^{13}$ and $R^{14}$.

11. The compound of claim 1, or a pharmaceutically acceptable salt thereof, wherein $R^5$ is phenyl substituted with one $C_{1-6}$-alkoxy.

12. The compound of claim 1, or a pharmaceutically acceptable salt thereof, wherein $R^8$ is phenyl substituted with $R^{15}$, $R^{16}$ and $R^{17}$.

13. The compound of claim 1, or a pharmaceutically acceptable salt thereof, wherein $R^{11}$ is selected from
i) phenyl substituted with $R^{18}$, $R^{19}$ and $R^{20}$, and
ii) pyridinyl substituted with $R^{18}$, $R^{19}$ and $R^{20}$.

14. The compound of claim 1, or a pharmaceutically acceptable salt thereof, wherein $R^{11}$ is phenyl substituted with $R^{18}$, $R^{19}$ and $R^{20}$.

15. The compound of claim 1, or a pharmaceutically acceptable salt thereof, wherein $R^{12}$ is selected from
i) H, and
ii) $C_{1-6}$-alkoxy.

16. The compound of claim 1, or a pharmaceutically acceptable salt thereof, wherein $R^{12}$ is H.

17. The compound of claim 1, or a pharmaceutically acceptable salt thereof, wherein $R^{13}$, $R^{14}$, $R^{17}$, $R^{20}$, $R^{24}$, $R^{25}$ and $R^{26}$ are each H.

18. The compound of claim 1, or a pharmaceutically acceptable salt thereof, wherein $R^{15}$ is selected from
i) H,
ii) cyano, and
iii) halogen.

19. The compound of claim 1, or a pharmaceutically acceptable salt thereof, wherein $R^{15}$ is halogen.

20. The compound of claim 1, or a pharmaceutically acceptable salt thereof, wherein $R^{16}$ is selected from
i) H, and
ii) halogen.

21. The compound of claim 1, or a pharmaceutically acceptable salt thereof, wherein $R^{16}$ is H.

22. The compound of claim 1, or a pharmaceutically acceptable salt thereof, wherein $R^{18}$ is selected from
i) halogen, and
ii) cyano.

23. The compound of claim 1, or a pharmaceutically acceptable salt thereof, wherein $R^{19}$ is selected from
i) H,
ii) cyano,
iii) $C_{1-6}$-alkyl, and
iv) halogen.

24. The compound of claim 1, or a pharmaceutically acceptable salt thereof, wherein $R^{19}$ is selected from
i) cyano, and
ii) halogen.

25. A compound according to claim 1, selected from the group consisting of:
(S)-4-((S)-2-((R)-2-(3,5-dichlorophenoxy)-3-phenylpropanamido)-3-phenyl propanamido)-2,2-difluoro-5-methyl-3-oxo-N-(2,2,2-trifluoroethyl)hexanamide;
(S)-4-((S)-2-((R)-2-(3,5-dichlorophenoxy)-3-phenylpropanamido)-2-phenylacetamido)-2,2-difluoro-5-methyl-N-(2-morpholinoethyl)-3-oxohexanamide;

(S)-4-((S)-2-((R)-2-(3,5-dichlorophenoxy)-3-phenylpropanamido)-2-(4-methoxyphenyl)acetamido)-2,2-difluoro-5-methyl-3-oxo-N-(2,2,2-trifluoroethyl)hexanamide;

(S)-4-((S)-2-((R)-3-(3-chlorophenyl)-2-(3,5-dichlorophenoxy)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3-chloro-5-methylphenoxy)-3-(3-chlorophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3-chlorophenoxy)-3-(3,4-dichlorophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((R)-3-(3-chlorophenyl)-2-(3,5-di cyanophenoxy)propanamido)-2-(4-methoxyphenyl)acetamido)-2,2-difluoro-5-methyl-3-oxo-N-(2,2,2-trifluoroethyl)hexanamide;

(S)-4-((S)-2-((R)-3-(3-chlorophenyl)-2-((5-chloropyridin-3-yl)oxy)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3-chlorophenoxy)-3-(3,5-dichlorophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((S)-3-(3-chlorophenyl)-2-(3,5-dichlorophenoxy)propanamido)-2-(4-methoxyphenyl)acetamido)-2,2-difluoro-5-methyl-3-oxo-N-(2,2,2-trifluoroethyl)hexanamide;

(S)-4-((S)-2-((S)-3-(3-chlorophenyl)-2-(3,5-dichlorophenoxy)propanamido)-2-phenylacetamido)-2,2-difluoro-5-methyl-3-oxo-N-(2,2,2-trifluoroethyl)hexanamide;

(S)-4-((S)-2-((R)-2-(3-chloro-5-cyanophenoxy)-3-(3-chlorophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3-chloro-5-cyanophenoxy)-3-(3-chlorophenyl)propanamido)-2-phenylacetamido)-2,2-difluoro-5-methyl-3-oxo-N-(2,2,2-trifluoroethyl)hexanamide;

(4S)-4-((2S)-2-(2-(3-chloro-5-cyanophenoxy)-3-(3-cyanophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3,5-dicyanophenoxy)-3-(3-fluorophenyl)propanamido)-2-(4-methoxyphenyl)acetamido)-2,2-difluoro-5-methyl-3-oxo-N-(2,2,2-trifluoroethyl)hexanamide;

(S)-4-((S)-2-((R)-2-(3-cyanophenoxy)-3-(3-fluorophenyl)propanamido)-2-(4-methoxyphenyl)acetamido)-2,2-difluoro-5-methyl-3-oxo-N-(2,2,2-trifluoroethyl)hexanamide; and (S)-4-((S)-2-((R)-2-(3-chlorophenoxy)-3-(3-fluorophenyl)propanamido)-2-(4-methoxyphenyl)acetamido)-2,2-difluoro-5-methyl-3-oxo-N-(2,2,2-trifluoroethyl)hexanamide;

or a pharmaceutically acceptable salt thereof.

26. A process to prepare a compound according to claim 1 comprising
i) the reaction of a compound of formula (III) with a compound of formula (IV)

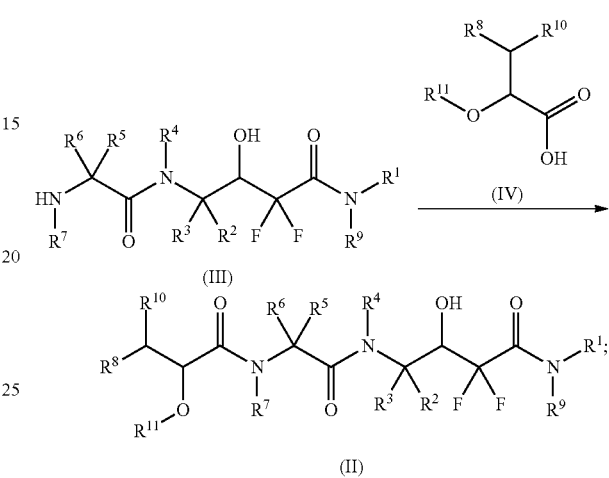

and
ii) the reaction of a compound of formula (II) in oxidative conditions

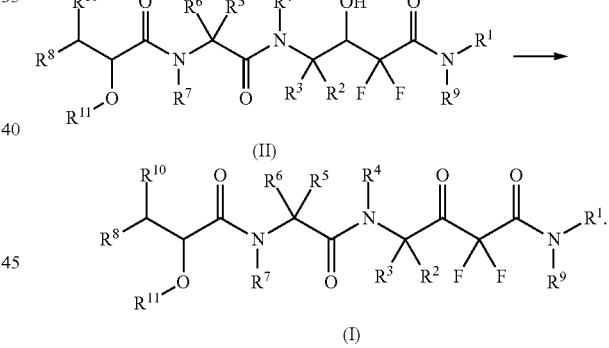

27. A pharmaceutical composition comprising a compound according to claim 1, or a pharmaceutically acceptable salt thereof, and a therapeutically inert carrier.

28. A method for the treatment of HtrA1-mediated ocular conditions selected from wet or dry age-related macular degeneration, geographic atrophy, diabetic retinopathy, retinopathy of prematurity and polypoidal choroidal vasculopathy, which method comprises administering an effective amount of a compound according to claim 1, or a pharmaceutically acceptable salt thereof.

* * * * *